US009162951B2

(12) United States Patent
Ryba et al.

(10) Patent No.: US 9,162,951 B2
(45) **Date of Patent: *Oct. 20, 2015**

(54) CONTINUOUS PROCESS FOR CONVERSION OF LIGNIN TO USEFUL COMPOUNDS

(71) Applicant: Chemtex Italia, S.p.A., Tortona, AL (US)

(72) Inventors: Steven Ryba, Wadsworth, OH (US); Aaron Murray, Chardon, OH (US); Guliz Arf Elliott, Northfield Center, OH (US); Dan Gastaldo, Middleburg Heights, OH (US)

(73) Assignee: Biochemtex S.p.A., Tortona (AL) (IT)

( * ) Notice: Subject to any disclaimer, the term of this patent is extended or adjusted under 35 U.S.C. 154(b) by 63 days.

This patent is subject to a terminal disclaimer.

(21) Appl. No.: 13/775,240

(22) Filed: Feb. 24, 2013

(65) Prior Publication Data

US 2013/0225855 A1 Aug. 29, 2013

Related U.S. Application Data

(60) Provisional application No. 61/603,217, filed on Feb. 24, 2012, provisional application No. 61/719,486, filed on Oct. 28, 2012, provisional application No. 61/751,919, filed on Jan. 13, 2013, provisional application No. 61/765,611, filed on Feb. 15, 2013, provisional application No. 61/765,402, filed on Feb. 15, 2013.

(51) Int. Cl.

| | |
|---|---|
| ***C07C 41/01*** | (2006.01) |
| ***C07C 37/54*** | (2006.01) |
| ***C07C 45/42*** | (2006.01) |
| ***C07C 1/20*** | (2006.01) |
| ***C07C 67/00*** | (2006.01) |
| ***C07C 29/09*** | (2006.01) |
| ***C08L 97/00*** | (2006.01) |
| ***B01D 21/00*** | (2006.01) |
| ***C07B 31/00*** | (2006.01) |
| ***C07C 45/59*** | (2006.01) |
| ***C07C 45/60*** | (2006.01) |
| ***C07C 29/00*** | (2006.01) |
| ***C08H 8/00*** | (2010.01) |

(52) U.S. Cl.

CPC ................ *C07C 37/54* (2013.01); *B01D 21/00* (2013.01); *C07B 31/00* (2013.01); *C07C 1/20* (2013.01); *C07C 29/00* (2013.01); *C07C 29/09* (2013.01); *C07C 41/01* (2013.01); *C07C 45/42* (2013.01); *C07C 45/59* (2013.01); *C07C 45/60* (2013.01); *C07C 67/00* (2013.01); *C08H 8/00* (2013.01); *C08L 97/005* (2013.01); *C07C 2101/08* (2013.01); *C07C 2101/10* (2013.01); *C07C 2101/14* (2013.01)

(58) Field of Classification Search

CPC ........................................................ C07C 4/01
USPC .......................................... 560/129; 568/630
See application file for complete search history.

(56) References Cited

U.S. PATENT DOCUMENTS

2010/0331560 A1* 12/2010 Borden ......................... 554/223

FOREIGN PATENT DOCUMENTS

| | | | |
|---|---|---|---|
| WO | 2011/061400 | A1 | 5/2011 |
| WO | 2011/117705 | A2 | 9/2011 |
| WO | 2012/174429 | A1 | 12/2012 |
| WO | 2013/011206 | A1 | 1/2013 |

OTHER PUBLICATIONS

U.S. Appl. No. 13/775,241, filed Feb. 24, 2013, Ryba et al.*
U.S. Appl. No. 13/775,239, filed Feb. 24, 2013, Ryba et al.*
Parveen Kumar et al., "Methods for Pretreatment of Lignocellulosic Biomass for Efficient Hydrolysis and Biofuel Production", Industrial & Engineering Chemistry Research, Apr. 15, 2009, pp. 3713-3729, vol. 48, No. 8, American Chemical Society, US.
Xingyu Wang et al., "Exploiting H-transfer reactions with RANEY Ni for upgrade of phenolic and aromatic biorefinery feeds under unusual, low-severity conditions", Energy & Environmental Science, Jan. 1, 2012, p. 8244, vol. 5, No. 8.
"KOV piston pumps with ball valves for high-pressure slurry pumping", Putzmeister, Jan. 1, 2010, pp. 47-1.
Kirk D.F. et al., "Gravity Concentration", Kirk-Othmer Encyclopedia of Chemical Technology, Jan. 1, 1980, pp. 1-29, vol. 12, John Wiley & Sons, New York, U.S.
De Jongh & R P P Rijs J A, "Pump Design", Arakis, Mar. 1, 2004, pp. 1-45.

* cited by examiner

*Primary Examiner* — Yong Chu
*Assistant Examiner* — Sonya Wright
(74) *Attorney, Agent, or Firm* — Edwin A. Sisson, Attorney at Law, LLC

(57) ABSTRACT

This specification discloses an operational continuous process to convert lignin as found in ligno-cellulosic biomass before or after converting at least some of the carbohydrates. The continuous process has been demonstrated to create a slurry comprised of lignin, raise the slurry comprised of lignin to ultra-high pressure, deoxygenate the lignin in a lignin conversion reactor over a catalyst which is not a fixed bed without producing char. The conversion products of the carbohydrates or lignin can be further processed into polyester intermediates for use in polyester preforms and bottles.

18 Claims, 9 Drawing Sheets

CONTINUOUS PROCESS FOR CONVERSION OF LIGNIN TO USEFUL COMPOUNDS

PRIORITY AND CROSS REFERENCES

This application claims the priority of U.S. Provisional Patent Application No. 61/603,217 filed 24 Feb. 2012, U.S. Provisional Patent Application No. 61/719,486 filed 28 Oct. 2012, U.S. Provisional Patent Application No. 61/751,919 filed 13 Jan. 2013, U.S. Provisional Patent Application No. 61/764,611 filed 14 Feb. 2013, U.S. Provisional Patent Application No. 61/765,402 filed 15 Feb. 2013, and WIPO Application No. PCT/US2013/027393 the teachings of all of which are incorporated in their entirety.

BACKGROUND

The conversion of lignin in batch processes using hydrogen and catalysts is known. For example, Boocock, D. G. B et al, "The Production of Synthetic Organic Liquids from Wood Using a Modified Nickel Catalyst" discloses exposing air dried poplar to hydrogen and Raney Nickel in a batch autoclave at 340° C. to 350° C. for 1 or 2 h to produce "oil products". However, according to Boocock et al, "[t]he use of Raney nickel has now been abandoned in favour of nickel from nickel salts . . . . "

The use of catalysts to recover lignin is also known. Zakzeski, Pieter C., et al; "The Catalytic Valorization of Lignin for the Production of Renewable Chemicals", 2010 is a comprehensive review of catalytic efforts to convert lignin.

While many have proposed theoretical continuous processes, the inventors are not aware of any disclosure which is enabling beyond a theoretical basis. For example, converting solid lignin presents significant handling problems as documented in PNNL-16079, September 2006.

"High-pressure feeding systems for biomass slurries have been recognized as a process development issue at least as long as the modern biomass conversion systems have been under development since the Arab oil embargo of 1973. The authors review the state of the art and various slurry pumping systems, the vast majority of which include ball check valves. Their conclusion is that high-pressure feeding remains a problem for small scale production but believe "the high-pressure feeding of biomass slurries should be more readily achieved at larger flow rates wherein the fibrous nature of the biomass would not be expected to bridge and plug the orifices and valves."

There exists therefore the need to provide a pumping and charging scheme for slurries.

An example of this is in the series of applications US 2011/0312051, US 2011/0312487, US 2011/0312488, US 2011/0313212, US 2011/0313210, US 2011/0313209, US 2011/0313208, and US 2011/0312050. These applications to common inventors propose a continuous process based only upon batch autoclave results demonstrating high catalytic selectivity to ethylene glycol. However, the high ethylene glycol yields depend upon the purity of the cellulose feedstock which will intuitively cleave into 3 units of ethylene glycol. Of the experiments listed, the experiments using a feedstock closest to a biomass feedstock as found in the industrial or natural environment is bleached pulp. However, bleached pulp only produced a yield of 37%. When hemicellulose is used (xylose), the results are expected to be shifted much more away from ethylene glycol to propylene glycol. While the continuous process is theoretically described, the application fails to disclose an enabling continuous process. For example, the disclosure states that "[m] aterials [of a continuous] process must be capable of being transported from a low pressure source into the reaction zone, and products must be capable of being transported from the reaction zone to the product recovery zone. Depending upon the mode of operation, residual solids, if any, must be capable of being removed from the reaction zone." This discloses the intuitively obvious requirement to operate a continuous process but the statement fails to teach one of ordinary skill how to achieve those requirements. Nowhere in the application is this essential problem discussed or solved. In fact, during the discussion of FIG. 2 of the publication, the temperature and pressure conditions are discussed without any disclosure as to how the slurry can be raised to the listed pressure of 1800 psig, or even 200 psig. When considering the transport problem, which, as of 2006, has existed since the oil embargo of 1973, a disclosure telling one of ordinary skill that transport of materials is critical can hardly be considered enabling.

These series of applications also disclose to keep the water in the reaction zone in the liquid phase. In the batch autoclave this occurs due to the sealed nature. However, it fails to disclose how this is done, or even if it can be done, in a continuous process.

In order to avoid the problems of pumping and charging as noted, but not solved, in the above applications and publications, dissolution of the lignin is proposed. WO 2011/117705 relies upon dissolving the lignin so that the material can be charged as a liquid taking full advantage of the check valve and high pressure liquid charging systems. In fact, according to WO 2011/117705, "the only limit [is] that the lignin fed to the hydrogenolysis reaction is well dissolved, at the feeding temperature, in said solvent."

There exists therefore the need for a properly enabling disclosure of how to continuously convert lignin which includes the handling, charging, and essential conditions for the process to be carried out. These conditions and steps are believed both novel and inventive and for the first time experimentally enabled.

SUMMARY

Disclosed in this specification is a method for separating lignin conversion products from catalyst particles during a continuous catalytic conversion of a lignin feedstock to lignin conversion products comprising the steps of:

a. conducting the continuous catalytic conversion of the lignin feedstock to the lignin conversion products in the presence of free catalyst particles in a lignin conversion reactor, with the lignin conversion reactor having a liquid phase and a gas phase with a liquid level at the interface between the liquid phase and the gas phase, and
b. removing the lignin conversion products from the lignin conversion reactor at a lignin conversion products removal velocity at a point in the lignin conversion reactor which is higher relative to gravity than the liquid level of the lignin conversion reactor wherein the lignin conversion products removal velocity is less than a settling velocity of the catalyst particles.

In one embodiment the lignin conversion products are removed from the lignin conversion reactor via a dip tube.

In one embodiment the lignin conversion products removal velocity is less than the settling velocity of at least 75% by weight of the catalyst particles. In another embodiment the lignin conversion products removal velocity is less than the settling velocity of at least 80% by weight of the catalyst particles. In another embodiment the lignin conversion products removal velocity is less than the settling velocity of at least 85% by weight of the catalyst particles. In yet another embodiment the lignin conversion products removal velocity is less than the settling velocity of at least 90% by weight of the catalyst particles. In still another embodiment the lignin conversion products removal velocity is less than the settling velocity of at least 95% by weight of the catalyst particles. In another embodiment the lignin conversion products removal velocity is less than the settling velocity of at least 100% by weight of the catalyst particles.

DETAILED DESCRIPTION

Figure 1:
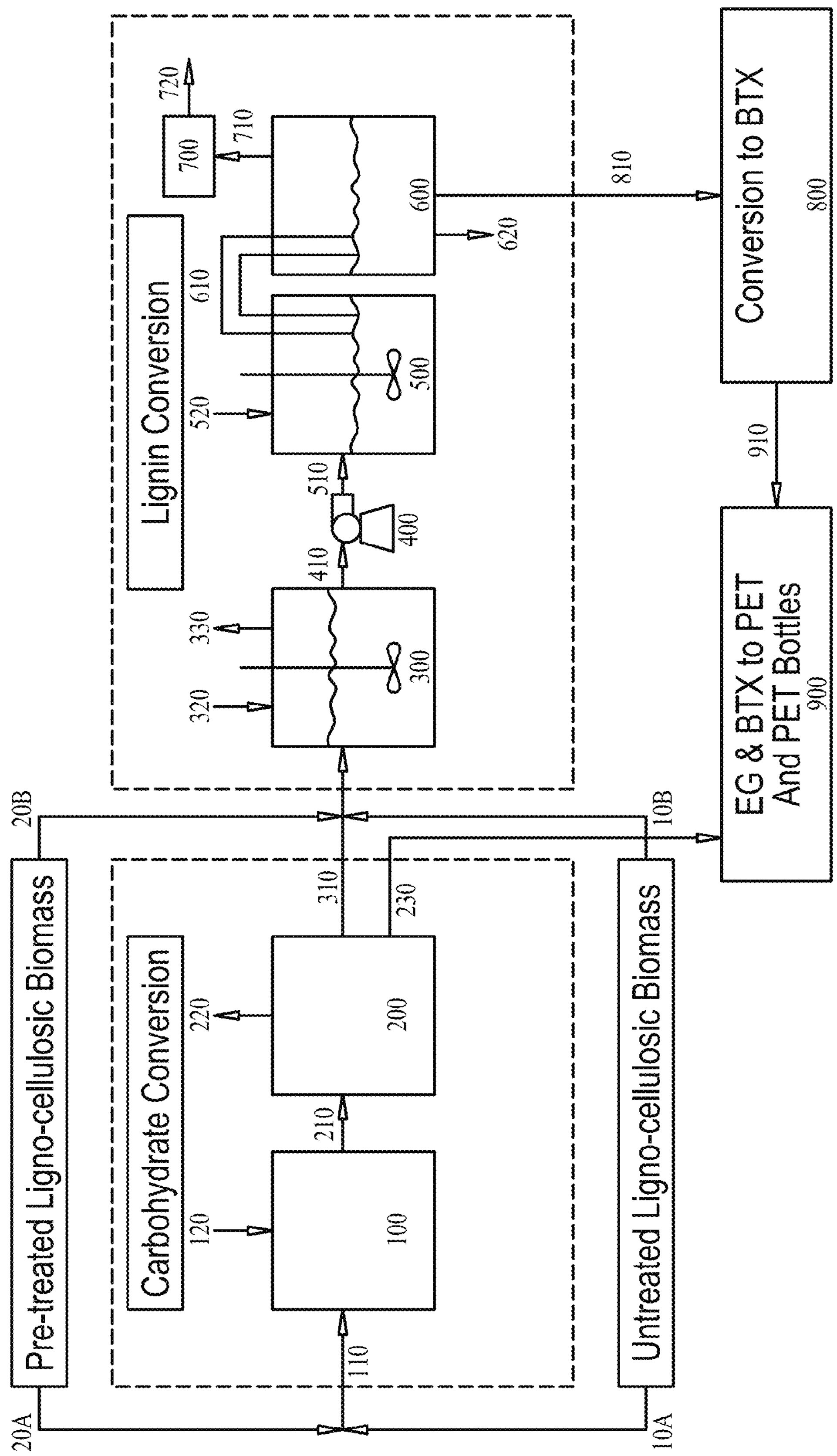
FIG. 1 is a schematic description of the unit operations of a fully integrated process for continuously converting ligno-cellulosic biomass feedstock to polyester bottles.
Figure 2:
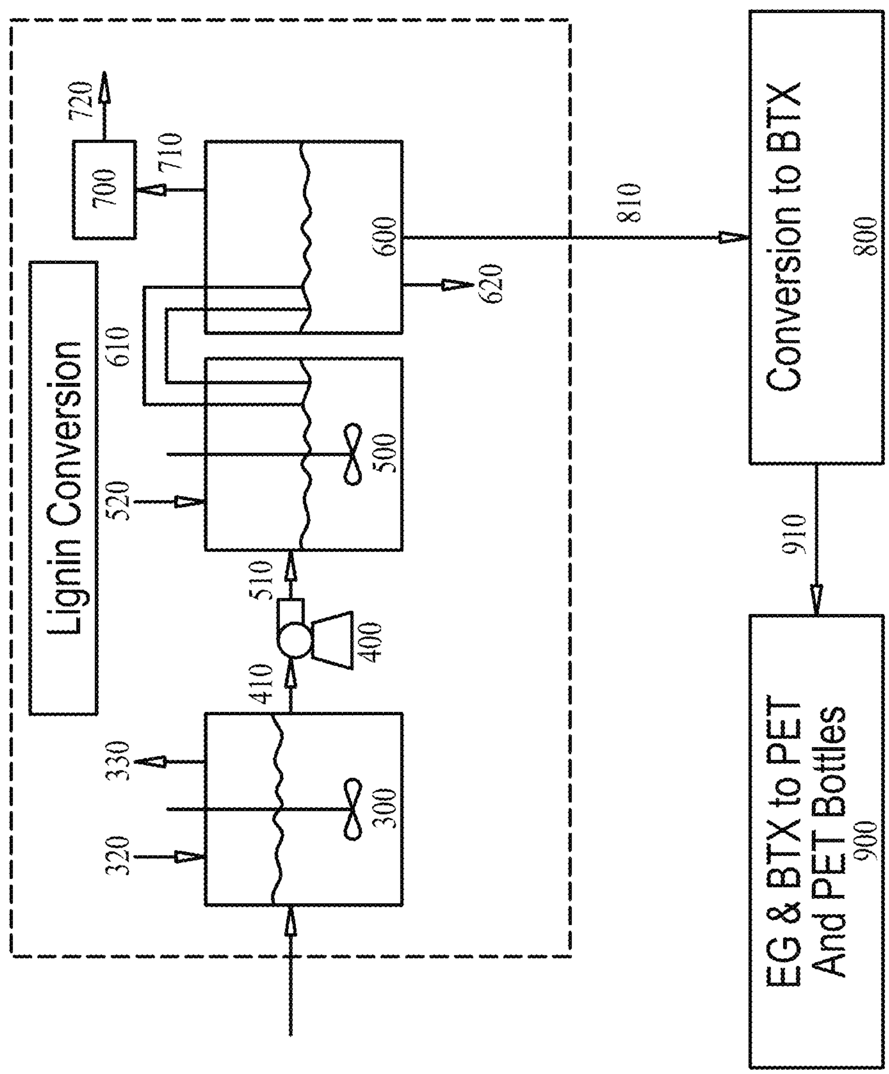
FIG. 2 shows a further embodiment of the process.

This specification is an enabling disclosure and an actual reduction to practice of a continuous lignin conversion process of high yields, in particular from biomass feedstock. Approximately 80% of the available lignin in the feedstock is recovered as usable products.

Although not apparent from the numbers, the disclosed process is a very high yield conversion process. In approximate terms, 1 kg of biomass feedstock used contained 50% lignin, 41% carbohydrates and 9% ash, by weight of the dry feed.

Demonstrated high lignin recovery of the process based upon 1 kg of feedstock are as follows:

50% by dry weight of the feedstock is not lignin and not used, as it is either destroyed or, in the case of ash, simply not available. Of the lignin remaining, 35-40% by weight of the lignin is oxygen which is removed from the process (deoxygenated). Thus, while 50% of the feedstock is lignin, 40% of that weight is unavailable lignin (oxygen), leaving only 30% of the total weight of the feedstock as the theoretical recoverable amount of lignin. The experiments below have recovered up to 24-26% of the feedstock by weight, or approximately 80% of the theoretically available lignin has been converted to usable oils.

As noted in the background section, many have proposed continuous lignin and biomass reactors developed on lignin conversion data from batch autoclaves. These previous disclosures have attempted to teach and enable a continuous process. However, these are non-enabling disclosures and generally inoperative as the processes fail to address the problems facing a continuous process.

As an example, the continuous process produced very little long chain aliphatic hydrocarbons, whereas the comparative batch process produced a significant amount of long chain aliphatic hydrocarbons. It is believed that the continuous process destroyed the carbohydrates to very low molecular weight, low boiling point molecules such as methane and carbon dioxide and removed them through the exit gas. In a batch process, these compounds are kept in the reactor and are believed to be further converted to long chain aliphatics (greater than 12 carbons). Therefore, in the continuous process of this disclosure, the amount of aliphatic carbons having a number of carbons greater than 11 expressed as a percent of the total weight of the conversion products is less than 10% by weight, with less than 8% by weight more preferred, with less than 5% by weight even more preferred with less than 2.5% by weight most preferred.

The above problem is just one of many encountered by the inventors when trying to create a continuous process using industrial ligno-cellulosic feedstocks and not model compounds. These problems make it impossible to predict and enably claim a theoretical continuous process on the basis of batch data or model compounds.

Not only does this specification fully enable one of ordinary skill to operate a continuous process to convert lignin to liquid oils, the specification also discloses the subsequent use of the oils to make a polyester bottle or container.

Lignin

The claimed process utilizes a feed or feedstock comprising lignin. It can also utilize a feedstock consisting of lignin, or a feedstock consisting essentially of lignin, or a feedstock comprising at least 95% lignin by weight.

Lignin does not have a single chemical structure. In fact, according to the Kirk Othmer Encyclopedia, the exact chemical structure of lignin, as it occurs in wood, is not known and because it is hard to extract from wood without changing its structure, the exact structure may never be known. While there are many variations of Lignin, the term lignin, as used in this specification, refers to any polymer comprising p-hydroxyphenyl units, syringyl units, and guaiacyl units.

While pure lignin, such as Organosolv, Acetosolv lignins may be used, the extraction of lignin from its natural origins is expensive using organic solvents with the attendant environmental issues. The robustness of the claimed process is established by the fact is the process is experimentally demonstrated on a continuous basis to convert lignin as lignin is found in a lignin-cellulosic biomass feedstock.

Lignin Cellulosic Biomass Feedstock

The lignin to be converted in this invention can be present as a feed or feedstock of natural ligno-cellulosic biomass comprising at least one carbohydrate and lignin. Depending upon how the natural ligno-cellulosic biomass is treated another embodiment of the feedstock may have the composition and unique decomposition temperatures and surface areas described below.

Because the feedstock may use naturally occurring ligno-cellulosic biomass, the stream will have relatively young carbon materials. The following, taken from ASTM D 6866-04 describes the contemporary carbon, which is that found in bio-based hydrocarbons, as opposed to hydrocarbons derived from oil wells, which was derived from biomass thousands of years ago. "[A] direct indication of the relative contribution of fossil carbon and living biospheric carbon can be as expressed as the fraction (or percentage) of contemporary carbon, symbol $f_C$. This is derived from $f_M$ through the use of the observed input function for atmospheric $^{14}C$ over recent decades, representing the combined effects of fossil dilution of the $^{14}C$ (minor) and nuclear testing enhancement (major). The relation between $f_C$ and $f_M$ is necessarily a function of time. By 1985, when the particulate sampling discussed in the cited reference [of ASTM D 6866-04, the teachings of which are incorporated by reference in their entirety] the $f_M$ ratio had decreased to ca. 1.2."

Fossil carbon is carbon that contains essentially no radiocarbon because its age is very much greater than the 5730 year half life of $^{14}C$. Modern carbon is explicitly 0.95 times the specific activity of SRM 4990b (the original oxalic acid radiocarbon standard), normalized to $\delta^{13}C=-19\%$. Functionally, the faction of modern carbon=(1/0.95) where the unit 1 is defined as the concentration of $^{14}C$ contemporaneous with 1950 [A.D.] wood (that is, pre-atmospheric nuclear testing) and 0.95 are used to correct for the post 1950 [A.D.] bomb $^{14}C$ injection into the atmosphere. As described in the analysis and interpretation section of the test method, a 100% $^{14}C$ indicates an entirely modern carbon source, such as the products derived from this process. Therefore, the percent $^{14}C$ of the product stream from the process will be at least 75%, with 85% more preferred, 95% even preferred and at least 99% even more preferred and at least 100% the most preferred. (The test method notes that the percent $^{14}C$ can be slightly greater than 100% for the reasons set forth in the method). These percentages can also be equated to the amount of contemporary carbon as well.

Therefore the amount of contemporary carbon relative to the total amount of carbon is preferred to be at least 75%, with 85% more preferred, 95% even more preferred and at least 99% even more preferred and at least 100% the most preferred. Correspondingly, each carbon containing compound in the reactor, which includes a plurality of carbon containing conversion products will have an amount of contemporary carbon relative to total amount of carbon is preferred to be at least 75%, with 85% more preferred, 95% even preferred and at least 99% even more preferred and at least 100% the most preferred.

In general, a natural or naturally occurring ligno-cellulosic biomass can be one feed stock for this process. Ligno-cellulosic materials can be described as follows:

Apart from starch, the three major constituents in plant biomass are cellulose, hemicellulose and lignin, which are commonly referred to by the generic term lignocellulose. Polysaccharide-containing biomasses as a generic term include both starch and ligno-cellulosic biomasses. Therefore, some types of feedstocks can be plant biomass, polysaccharide containing biomass, and ligno-cellulosic biomass.

Polysaccharide-containing biomasses according to the present invention include any material containing polymeric sugars e.g. in the form of starch as well as refined starch, cellulose and hemicellulose.

Relevant types of naturally occurring biomasses for deriving the claimed invention may include biomasses derived from agricultural crops selected from the group consisting of starch containing grains, refined starch; corn stover, bagasse, straw e.g. from rice, wheat, rye, oat, barley, rape, sorghum; softwood e.g. *Pinus sylvestris, Pinus radiate*; hardwood e.g. *Salix* spp. *Eucalyptus* spp.; tubers e.g. beet, potato; cereals from e.g. rice, wheat, rye, oat, barley, rape, sorghum and corn; waste paper, fiber fractions from biogas processing, manure, residues from oil palm processing, municipal solid waste or the like. Although the experiments are limited to a few examples of the enumerated list above, the invention is believed applicable to all because the characterization is primarily to the unique characteristics of the lignin and surface area.

The ligno-cellulosic biomass feedstock used to derive the composition is preferably from the family usually called grasses. The proper name is the family known as Poaceae or Gramineae in the Class Liliopsida (the monocots) of the flowering plants. Plants of this family are usually called grasses, or, to distinguish them from other graminoids, true grasses. Bamboo is also included. There are about 600 genera and some 9,000-10,000 or more species of grasses (Kew Index of World Grass Species).

Poaceae includes the staple food grains and cereal crops grown around the world, lawn and forage grasses, and bamboo. Poaceae generally have hollow stems called culms, which are plugged (solid) at intervals called nodes, the points along the culm at which leaves arise. Grass leaves are usually alternate, distichous (in one plane) or rarely spiral, and parallel-veined. Each leaf is differentiated into a lower sheath which hugs the stem for a distance and a blade with margins usually entire. The leaf blades of many grasses are hardened with silica phytoliths, which helps discourage grazing animals. In some grasses (such as sword grass) this makes the edges of the grass blades sharp enough to cut human skin. A membranous appendage or fringe of hairs, called the ligule, lies at the junction between sheath and blade, preventing water or insects from penetrating into the sheath.

Grass blades grow at the base of the blade and not from elongated stem tips. This low growth point evolved in response to grazing animals and allows grasses to be grazed or mown regularly without severe damage to the plant.

Flowers of Poaceae are characteristically arranged in spikelets, each spikelet having one or more florets (the spikelets are further grouped into panicles or spikes). A spikelet consists of two (or sometimes fewer) bracts at the base, called glumes, followed by one or more florets. A floret consists of the flower surrounded by two bracts called the lemma (the external one) and the palea (the internal). The flowers are usually hermaphroditic (maize, monoecious, is an exception) and pollination is almost always anemophilous. The perianth is reduced to two scales, called lodicules, that expand and contract to spread the lemma and palea; these are generally interpreted to be modified sepals.

The fruit of Poaceae is a caryopsis in which the seed coat is fused to the fruit wall and thus, not separable from it (as in a maize kernel).

There are three general classifications of growth habit present in grasses; bunch-type (also called caespitose), stoloniferous and rhizomatous.

The success of the grasses lies in part in their morphology and growth processes, and in part in their physiological diversity. Most of the grasses divide into two physiological groups, using the C3 and C4 photosynthetic pathways for carbon fixation. The C4 grasses have a photosynthetic pathway linked to specialized Kranz leaf anatomy that particularly adapts them to hot climates and an atmosphere low in carbon dioxide.

C3 grasses are referred to as "cool season grasses" while C4 plants are considered "warm season grasses". Grasses may be either annual or perennial. Examples of annual cool season are wheat, rye, annual bluegrass (annual meadowgrass, *Poa annua* and oat). Examples of perennial cool season are orchard grass (cocksfoot, *Dactylis glomerata*), fescue (*Festuca* spp), Kentucky Bluegrass and perennial ryegrass (*Lolium perenne*). Examples of annual warm season are corn, sudangrass and pearl millet. Examples of Perennial Warm Season are big bluestem, indian grass, bermuda grass and switch grass.

One classification of the grass family recognizes twelve subfamilies: These are 1) anomochlooideae, a small lineage of broad-leaved grasses that includes two genera (*Anomochloa, Streptochaeta*); 2) Pharoideae, a small lineage of grasses that includes three genera, including *Pharus* and *Leptaspis;* 3) Puelioideae a small lineage that includes the African genus *Puelia;* 4) Pooideae which includes wheat, barley, oats, brome-grass (*Bronnus*) and reed-grasses (*Calamagrostis*); 5) Bambusoideae which includes bamboo; 6) Ehrhartoideae, which includes rice, and wild rice; 7) Arundinoideae, which includes the giant reed and common reed; 8) Centothecoideae, a small subfamily of 11 genera that is sometimes included in Panicoideae; 9) Chloridoideae including the lovegrasses (*Eragrostis*, ca. 350 species, including teff), dropseeds (*Sporobolus*, some 160 species), finger millet (*Eleusine coracana* (L.) Gaertn.), and the muhly grasses (*Muhlenbergia*, ca. 175 species); 10) Panicoideae including panic grass, maize, sorghum, sugar cane, most millets, fonio and bluestem grasses; 11) Micrairoideae and 12) Danthoniodieae including pampas grass; with *Poa* which is a genus of about 500 species of grasses, native to the temperate regions of both hemispheres.

Agricultural grasses grown for their edible seeds are called cereals. Three common cereals are rice, wheat and maize (corn). Of all crops, 70% are grasses.

Sugarcane is the major source of sugar production. Grasses are used for construction. Scaffolding made from bamboo is able to withstand typhoon force winds that would break steel scaffolding. Larger bamboos and *Arundo donax* have stout culms that can be used in a manner similar to timber, and grass roots stabilize the sod of sod houses. *Arundo* is used to make reeds for woodwind instruments, and bamboo is used for innumerable implements.

Another naturally occurring ligno-cellulosic biomass feedstock may be woody plants or woods. A woody plant is a plant that uses wood as its structural tissue. These are typically perennial plants whose stems and larger roots are reinforced with wood produced adjacent to the vascular tissues. The main stem, larger branches, and roots of these plants are usually covered by a layer of thickened bark. Woody plants are usually either trees, shrubs, or lianas. Wood is a structural cellular adaptation that allows woody plants to grow from above ground stems year after year, thus making some woody plants the largest and tallest plants.

These plants need a vascular system to move water and nutrients from the roots to the leaves (xylem) and to move sugars from the leaves to the rest of the plant (phloem). There are two kinds of xylem: primary that is formed during primary growth from procambium and secondary xylem that is formed during secondary growth from vascular cambium.

What is usually called "wood" is the secondary xylem of such plants.

The two main groups in which secondary xylem can be found are:

1) conifers (Coniferae): there are some six hundred species of conifers. All species have secondary xylem, which is relatively uniform in structure throughout this group. Many conifers become tall trees: the secondary xylem of such trees is marketed as softwood.
2) angiosperms (Angiospermae): there are some quarter of a million to four hundred thousand species of angiosperms. Within this group secondary xylem has not been found in the monocots (e.g. Poaceae). Many non-monocot angiosperms become trees, and the secondary xylem of these is marketed as hardwood.

The term softwood useful in this process is used to describe wood from trees that belong to gymnosperms. The gymnosperms are plants with naked seeds not enclosed in an ovary. These seed "fruits" are considered more primitive than hardwoods. Softwood trees are usually evergreen; bear cones, and have needles or scale like leaves. They include conifer species e.g. pine, spruces, firs, and cedars. Wood hardness varies among the conifer species.

The term hardwood useful for this process is used to describe wood from trees that belong to the angiosperm family. Angiosperms are plants with ovules enclosed for protection in an ovary. When fertilized, these ovules develop into seeds. The hardwood trees are usually broad-leaved; in temperate and boreal latitudes they are mostly deciduous, but in tropics and subtropics mostly evergreen. These leaves can be either simple (single blades) or they can be compound with leaflets attached to a leaf stem. Although variable in shape all hardwood leaves have a distinct network of fine veins. The hardwood plants include e.g. Aspen, Birch, Cherry, Maple, Oak and Teak.

Therefore a preferred naturally occurring ligno-cellulosic biomass may be selected from the group consisting of the grasses and woods. Another preferred naturally occurring ligno-cellulosic biomass can be selected from the group consisting of the plants belonging to the conifers, angiosperms, Poaceae and families. Another preferred naturally occurring ligno-cellulosic biomass may be that biomass having at least 10% by weight of it dry matter as cellulose, or more preferably at least 5% by weight of its dry matter as cellulose.

The carbohydrate(s) comprising the invention is selected from the group of carbohydrates based upon the glucose, xylose, and mannose monomers and mixtures thereof.

The feedstock comprising lignin can be naturally occurring ligno-cellulosic biomass that has been ground to small particles, or one which has been further processed. One process for creating the feedstock comprising lignin, comprises the following steps.

Preferable Pretreatment

It has been theorized that pretreatment of the feedstock is a solution to the challenge of processing an insoluble solid feedstock comprising lignin or polysaccharides in a pressurized environment. According to US 2011/0312051, sizing, grinding, drying, hot catalytic treatment and combinations thereof are suitable pretreatment of the feedstock to facilitate the continuous transporting of the feedstock. While not presenting any experimental evidence, US 2011/0312051 claims that mild acid hydrolysis of polysaccharides, catalytic hydrogenation of polysaccharides, or enzymatic hydrolysis of polysaccharides are all suitable to create a transportable feedstock. US 2011/0312051 also claims that hot water treatment, steam treatment, thermal treatment, chemical treatment, biological treatment, or catalytic treatment may result in lower molecular weight polysaccharides and depolymerized lignins that are more easily transported as compared to the untreated ones. While this may help transport, there is no disclosure or solution to how to pressurize the solid/liquid slurry resulting from the pre-treatment. In fact, as the inventors have learned the conventional wisdom and conventional systems used for pressuring slurries failed when pre-treated ligno-cellulosic biomass feedstock is used.

In the integrated second generation industrial operations, pre-treatment is often used to ensure that the structure of the ligno-cellulosic content is rendered more accessible to the catalysts, such as enzymes, and at the same time the concentrations of harmful inhibitory by-products such as acetic acid, furfural and hydroxymethyl furfural remain substantially low. There are several strategies to achieve increased accessibility, many of which may yet be invented.

The current pre-treatment strategies imply subjecting the ligno-cellulosic biomass material to temperatures between 110-250° C. for 1-60 min e.g.:

Hot water extraction

Multistage dilute acid hydrolysis, which removes dissolved material before inhibitory substances are formed Dilute acid hydrolyses at relatively low severity conditions Alkaline wet oxidation Steam explosion.

A preferred pretreatment of a naturally occurring ligno-cellulosic biomass includes a soaking of the naturally occurring ligno-cellulosic biomass feedstock and a steam explosion of at least a part of the soaked naturally occurring ligno-cellulosic biomass feedstock.

The soaking occurs in a substance such as water in either vapor form, steam, or liquid form or liquid and steam together, to produce a product. The product is a soaked biomass containing a first liquid, with the first liquid usually being water in its liquid or vapor form or some mixture.

This soaking can be done by any number of techniques that expose a substance to water, which could be steam or liquid or mixture of steam and water, or, more in general, to water at high temperature and high pressure. The temperature should be in one of the following ranges: 145 to 165° C., 120 to 210° C., 140 to 210° C., 150 to 200° C., 155 to 185° C., 160 to 180° C. Although the time could be lengthy, such as up to but less than 24 hours, or less than 16 hours, or less than 12 hours, or less than 9 hours, or less than 6 hours; the time of exposure is preferably quite short, ranging from 1 minute to 6 hours, from 1 minute to 4 hours, from 1 minute to 3 hours, from 1 minute to 2.5 hours, more preferably 5 minutes to 1.5 hours, 5 minutes to 1 hour, 15 minutes to 1 hour.

If steam is used, it is preferably saturated, but could be superheated. The soaking step can be batch or continuous, with or without stirring. A low temperature soak prior to the high temperature soak can be used. The temperature of the low temperature soak is in the range of 25 to 90° C. Although the time could be lengthy, such as up to but less than 24 hours, or less than 16 hours, or less than 12 hours, or less than 9 hours or less than 6 hours; the time of exposure is preferably quite short, ranging from 1 minute to 6 hours, from 1 minute to 4 hours, from 1 minute to 3 hours, from 1 minute to 2.5 hours, more preferably 5 minutes to 1.5 hours, 5 minutes to 1 hour, 15 minutes to 1 hour.

Either soaking step could also include the addition of other compounds, e.g. $H_2SO4$, $NH_3$, in order to achieve higher performance later on in the process. However, it is preferred that acid, base or halogens not be used anywhere in the process or pre-treatment. The feedstock is preferably void of added sulfur, halogens, or nitrogen. The amount of sulfur, if present, in the composition is in the range of 0 to 1% by dry weight of the total composition. Additionally, the amount of total halogens, if present, are in the range of 0 to 1% by dry weight of the total composition. By keeping halogens from the feedstock, there are no halogens in the lignin conversion products.

The product comprising the first liquid is then passed to a separation step where the first liquid is separated from the soaked biomass. The liquid will not completely separate so that at least a portion of the liquid is separated, with preferably as much liquid as possible in an economic time frame. The liquid from this separation step is known as the first liquid stream comprising the first liquid. The first liquid will be the liquid used in the soaking, generally water and the soluble species of the feedstock. These water soluble species are glucan, xylan, galactan, arabinan, glucolygomers, xyloolygomers, galactolygomers and arabinolygomers. The solid biomass is called the first solid stream as it contains most, if not all, of the solids.

The separation of the liquid can again be done by known techniques and likely some which have yet to be invented. A preferred piece of equipment is a press, as a press will generate a liquid under high pressure.

The first solid stream is then steam exploded to create a steam exploded stream, comprising solids and a second liquid. Steam explosion is a well known technique in the biomass field and any of the systems available today and in the future are believed suitable for this step. The severity of the steam explosion is known in the literature as Ro, and is a function of time and temperature and is expressed as $$Ro=t\exp[(T-100)/14.75]$$

with temperature, T expressed in Celsius and time, t, expressed in common units.

The formula is also expressed as Log(Ro), namely $$\mathrm{Log}(Ro)=Ln(t)+[(T-100)/14.75].$$

Log(Ro) is preferably in the ranges of 2.8 to 5.3, 3 to 5.3, 3 to 5.0 and 3 to 4.3.

The steam exploded stream may be optionally washed at least with water and there may be other additives used as well. It is conceivable that another liquid may be used in the future, so water is not believed to be absolutely essential. At this point, water is the preferred liquid and if water is used, it is considered the third liquid. The liquid effluent from the optional wash is the third liquid stream. This wash step is not considered essential and is optional.

The washed exploded stream is then processed to remove at least a portion of the liquid in the washed exploded material. This separation step is also optional. The term at least a portion is removed, is to remind one that while removal of as much liquid as possible is desirable (pressing), it is unlikely that 100% removal is possible. In any event, 100% removal of the water is not desirable since water is needed for the subsequent hydrolysis reaction. The preferred process for this step is again a press, but other known techniques and those not invented yet are believed to be suitable. The products separated from this process are solids in the second solid stream and liquids in the second liquid stream.

The steam exploded stream is then subjected to hydrolysis to create a hydrolyzed stream. Optionally at least a part of the liquid of the first liquid stream is added to the steam exploded stream. Also, water is optionally added. Hydrolysis of the steam exploded stream is realized by contacting the steam exploded stream with a catalyst. Enzymes and enzyme composition is the preferred catalyst. While laccase, an enzyme known to alter lignin, may be used, the composition is preferably void of at least one enzyme which converts lignin. A preferred hydrolysis of the steam exploded stream comprises the step of:

A) Contacting the steam exploded stream with at least a portion of a solvent, the solvent comprised of water soluble hydrolyzed species; wherein at least some of the water soluble hydrolyzed species are the same as the water soluble hydrolyzed species obtainable from the hydrolysis of the steam exploded stream;

B) maintaining the contact between the steam exploded stream and the solvent at a temperature in the range of 20° C. to 200° C. for a time in the range of 5 minutes to 72 hours to create a hydrolyzed stream from the steam exploded stream.

The hydrolyzed stream is comprised of carbohydrate monomers selected from the group consisting of glucose, xylose, and mannose.

The hydrolyzed stream is subjected to fermentation to create a fermented stream comprised of the composition and water. The fermentation is performed by means of addition of yeast or yeast composition to the hydrolyzed stream.

Eventually hydrolysis and fermentation can be performed simultaneously, according to the well known technique of simultaneous saccharification and fermentation (SSF).

The composition derived from naturally occurring ligno-cellulosic biomass is separated from the water in the fermented stream. The separation of the liquid can be done by known techniques and likely some which have yet to be invented. A preferred piece of equipment is a press.

The composition is different from naturally occurring ligno-cellulosic biomass in that it has a large surface area as calculated according to the standard Brunauer, Emmett and Teller (BET) method.

The BET surface area of the dry composition is at least 4 $m^2$/gm more preferably in the range of 4 to 80 $m^2$/gm, with 4 to 50 $m^2$/gm being more preferable, 4 to 25 $m^2$/gm being even more preferred, and 4 to 15 $m^2$/gm being even more preferred and 4 to 12 $m^2$/gm being the most preferred.

The composition is further characterized by the peaks generated during a thermal gravimetric analysis, known as TGA.

In thermogravimetric analysis, the plot of the weight with respect to temperature and the plot of the first derivative of weight with respect to temperature are commonly used.

If the decomposition of the material or of a component of the material occurs in a specific range of temperature, the plot of the first derivative of weight with respect to temperature presents a maximum in the specific range of temperature, defined also as first derivative peak. The value of temperature corresponding to the first derivative peak is considered the decomposition temperature of the material or of that component of the material.

The material is a composition of many components, which decompose in different specific temperature ranges, the plot of the first derivative of weight with respect to temperature presents first derivative peaks associated to the decomposition of each component in each specific temperature range. The temperature values corresponding to the first derivative peaks are considered the decomposition temperatures of each component of the material.

As a general rule, a maximum is located between two minima. The values of temperature corresponding to the minima are considered as the initial decomposition temperature and the final decomposition temperature of the decomposition temperature range of the component whose decomposition temperature corresponds to the first derivative peak comprised between the two minima. In this way, a derivative peak corresponds to decomposition temperature range. The weight loss of the material in the range between the initial decomposition temperature and the final decomposition temperature is associated to the decomposition of that component of the material and to the first derivative peak.

Should the naturally occurring ligno-cellulosic biomass used to derive the lignin composition be a mixture of different species of grasses or plants or other materials, then the mixture of the naturally occurring ligno-cellulosic biomass is what should be used for the comparison with the material from which the composition was derived.

The composition created has the characteristics that temperature corresponding to the maximum value of the first lignin decomposition peak is less than the temperature corresponding to the maximum value of the first lignin decomposition peak of the naturally occurring ligno-cellulosic biomass. This difference is marked with the maximum value of the first lignin decomposition peak being less than the temperature corresponding to the maximum value of the first lignin decomposition peak of the naturally occurring ligno-cellulosic biomass by a value selected from the group consisting of at least 10° C., at least 15° C., at least 20° C., and at least 25° C.

This reduction in the maximum value of the first lignin decomposition temperature can be compared to the maximum value of the first lignin decomposition temperature after pre-treatment.

Additionally, the absolute mass on a dry basis associated with the first lignin decomposition peak of the claimed lignin composition is greater than the absolute mass on a dry basis of the second lignin decomposition peak. While for *Arundo donax*, the absolute mass of the first decomposition temperature of the naturally occurring ligno-cellulosic biomass is greater than the absolute mass of the second decomposition temperature of the naturally occurring ligno-cellulosic biomass, this is not true for many ligno-cellulosic biomasses such as corn stover and wheat straw. However, after conversion, the lignin composition derived from these biomasses has a mass on a dry basis associated with the first lignin decomposition temperature that is greater than the mass on a dry basis associated with the second lignin decomposition temperature.

The feedstock can be further characterized by comparing the temperature associated with the maximum value of the first lignin decomposition range with the temperature associated with the maximum value of the first lignin decomposition range of the ligno-cellulosic biomass used to derive the feedstock.

The feedstock can also be further characterized by the relative amount of carbohydrates, which include glucans and xylans, present on a dry basis. The composition may have the amount of total carbohydrates present in the composition in the range of 10 to 60% of the dry weight of the composition, with 10 to 40% more preferred with 5 to 35% even most preferred. Provided, of course, that the amount of total lignin present in the composition is in the range of 30 to 80% of the dry weight of the composition and the weight percent of the carbohydrates plus the weight percent of the lignin is less than 100% of the dry weight of the feedstock.

Because the composition of the feedstock comprising lignin may vary with the starting material from which it is derived, the naturally occurring ligno-cellulosic biomass from which the feedstock is derived can be selected from the group consisting of the grasses and food crops.

Slurry Creation

Lignin may be charged to a lignin conversion reactor (500) as a solid slurried in a liquid. In a preferred embodiment the liquid may comprise water. In another embodiment, the liquid may comprise a hydrogen donor. The use of hydrogen donors is well known and described in Wang, X, and Rinaldi, R.; "Exploiting H-Transfer reactions with RANEY® Ni for upgrade of phenolic and aromatic biorefinery feeds under unusual, low severity conditions:", Energy Environ. Sci., 2012, 5, 8244

It has been discovered that a slurry comprised of lignin has several unique characteristics making it difficult to create, maintain and handle, and in many instances a slurry comprised of lignin behaves in the opposite manner of traditional slurries.

The solid content of a slurry comprised of lignin should be in the range of about 1 to 70% by weight with 5 to 35% by weight solids content more preferred. Traditionally, slurries are easier to maintain when the solids content is low. Surprisingly, a slurry comprised of lignin is easier to maintain when the solids content is high (greater than 20% by weight solids).

The particle size of the slurry comprised of lignin should be such that the number average size is in the range of less than 200 micron with less than 150 micron being preferred and less than 100 micron being most preferred. Particle size reduction is not necessary when the feedstock comprising lignin has been steam exploded. However, particle size reduction is considered necessary if the practitioner is starting with naturally occurring lignin, such as wood chips.

No surfactants or emulsifying agents are needed, but they can be used.

There are several strategies for creating a slurry comprised of lignin depending upon the manufacturing location of the claimed process. If the lignin conversion is co-sited with the pre-treatment or carbohydrate conversion of the ligno-cellulosic biomass (10), then the lignin may already be present in a slurry form, often called the stillage or stillage lignin, with little or no water soluble sugars, or void of water soluble sugars. When the ligno-cellulosic biomass (10) is passed through the pre-treatment or carbohydrate conversion process first, the water soluble sugars are converted to species other than sugars. The water soluble sugars will have been washed off, extracted or converted by the enzymes or catalysts to species other than sugars, leaving the bottoms which are comprised of lignin and unconverted, insoluble carbohydrates, many of which are still bound with the lignin. These bottoms are void of or substantially void of free water soluble sugars.

In this iterated embodiment, the bottoms, (or stillage or stillage lignin as it is often called), of the sugar or carbohydrate conversion process, (e.g. fermentation), are passed directly to a next process which could further remove more carbohydrates; or the bottoms are passed directly to the lignin conversion process described herein. In this manner, the water from the carbohydrate conversion process which would otherwise have to be treated via expensive waste water treatment plant(s) is used as a slurry liquid to maintain or create the slurry comprised of lignin to feed the lignin conversion process. The stillage lignin, which is the slurry liquid removed from the carbohydrate conversion process comprising the lignin, is then cleaned in situ by the hydrogen of the lignin conversion process while at the same time, converting the lignin. As described later, the slurry liquid coming from the lignin conversion process will have significantly less total biochemical oxygen demand, also known as BOD's, and/or chemical oxygen demand, also known as COD's, relative to the amounts of BOD's and COD's in the incoming slurry liquid from the stillage lignin, thus reducing the amount of, and cost of waste water treatment needed before releasing the slurry liquid to the environment. The BOD's and COD's have been chemically destroyed by the conditions of the lignin conversion process.

In a further refinement, at least a portion of the slurry liquid from the lignin conversion process can be used as make up water or steam in a pre-treatment process, thus significantly reducing the amount and cost of water treatment. (See FIG. 3)

Figure 3:
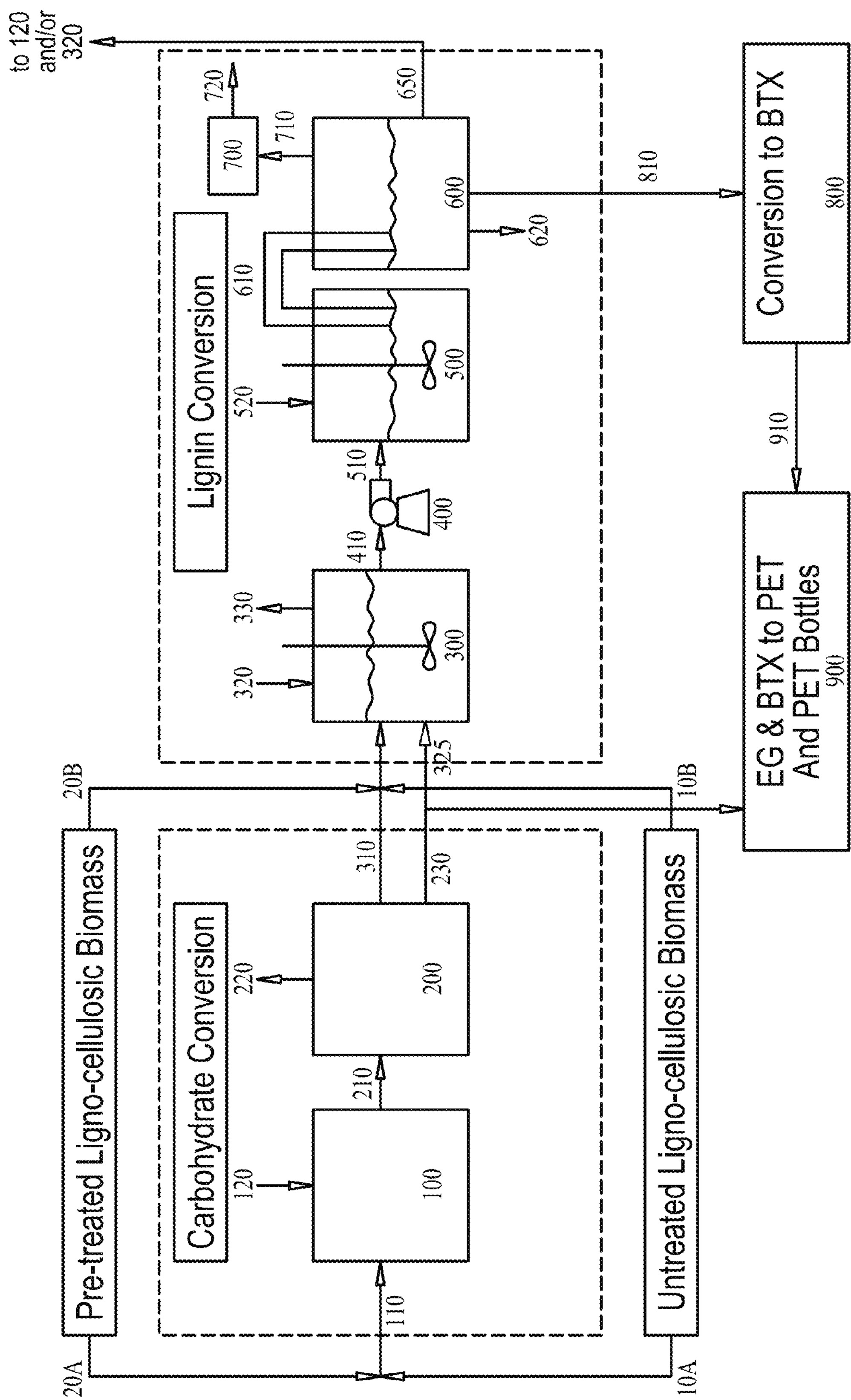
FIG. 3 shows an embodiment with at least a portion of the water from the lignin conversion process reused in the pretreatment or slurry creation step of an integrated facility.

This schematic is demonstrated in FIG. 3, wherein the ligno-cellulosic biomass (10) enters the pre-treatment process and the pre-treated ligno-cellulosic biomass is passed to the carbohydrate conversion process, in this instance fermentation. In the carbohydrate conversion process, the sugars are converted to the final product or products. It is preferable to introduce the slurry liquid from the lignin conversion process (620), prior to or simultaneously with the steam explosion step of the pretreatment process.

The bottoms, or stillage, comprising the lignin, slurry liquid, and possibly carbohydrates, is passed to the slurry creation step, (300). If the stillage lignin is a sufficiently stable slurry and of desired concentrations, (e.g. solids, buffers, pH), it can be passed directly to (400), the slurry pump, without any further treatment, e.g. water dilution or water reduction, agitation, vacuum.

If adjustments are needed, the slurry comprised of lignin is brought to the optimum slurry conditions by adjusting the solids concentration under agitation and optionally vacuum. Usually this is under high shear agitation of the slurry comprised of lignin.

In some embodiments, the bottoms of the carbohydrate conversion process will be shipped to a different location for the lignin conversion. While it is possible to ship the already slurried stillage, the cost of shipping water may make shipping cost prohibitive. In this instance, it is anticipated that the feedstock comprised of lignin will be shipped as a solid and often dry with as much water having been removed as possible; usually by a filter press, drying, or both. Oftentimes, the solid feedstock comprising lignin will be chilled or even frozen to prevent microbial growth during shipment or storage. The slurry liquid from the dewatering process is often sent to waste water treatment where it is cleaned to remove BOD's and COD's, and then released to the environment or reused in parts of the pre-treatment process. It is this external treatment step which can be minimized or reduced by re-using or recycling at least a portion of the slurry liquid from the lignin conversion process.

It has been directly observed that the feedstock comprising lignin is excessively intractable and the particles are very difficult to separate. This is particularly the case when the feedstock comprising lignin has been subjected to dewatering pressure to dewater, as in a filter press. Visible light microscopic examination shows the feedstock comprising lignin to have tendrils with tentacles and hooks, much like Velcro®.

As stated earlier, if the feedstock after the carbohydrate conversion step is already a slurry, it may be possible to add the slurry directly to the process without further treatment. However, generally this is not expected. After carbohydrate conversion, there is likely to be trapped gasses in the stillage lignin which should be removed.

If the lignin conversion is not co-sited with the pre-treatment or fermentation of the ligno-cellulosic biomass (10), then one strategy for creating the slurry comprised of lignin is to use a machine capable of applying high shear forces and apply high shear forces to the unslurried solid feedstock comprising lignin. High shear forces may be achieved by feeding the solid feedstock comprising lignin through a compounder. Preferred compounder embodiments include a twin screw co-rotating screws compounder, a twin screw counter-rotating screws compounder, an extruder, a banbury, or another device known for imparting mechanical forces to the material processed through it.

The amount of mechanical forces required is related to the amount of energy required to make the solid feedstock comprising lignin readily dispersible. The more mechanical forces applied to the solid feedstock comprising lignin, the easier the dispersion. The amount of mechanical forces required can be determined iteratively by comparing the energy consumed with the energy required to disperse the resulting solid into the slurry liquid of the slurry. Techniques to vary the amount and type of mechanical forces applied to the solid feedstock comprising lignin depend upon the equipment and are well known in the art to those familiar with the particular machine being used.

A slurry liquid can be added to the solid feedstock comprising lignin to produce a slurry comprised of lignin. It is preferred that the slurry liquid be added to the solid feedstock comprising lignin after exiting the compounder. In this regard, the solid feedstock comprising lignin is void of free liquid meaning that free liquid comprises less than 5% of the weight of the composition with no free liquid being preferred. In another embodiment, the slurry liquid may be added to the solid feedstock comprising lignin in the compounder. In a preferred embodiment the slurry liquid comprises water. In another embodiment, the slurry liquid may comprise a hydrogen donor. It should be noted that for the purposes of this specification, the slurry liquid is also known as a carrier liquid as well.

The amount of energy consumed by the compounder necessary to create a solid feedstock comprising lignin that is readily dispersible into a slurry liquid and/or has a low viscosity when dispersed into a slurry liquid can be determined by measuring the torque. The solid feedstock comprising lignin is readily dispersed into a slurry liquid when the amount of torque required to disperse the solid feedstock comprising lignin into the slurry liquid in the absence of a hydrolysis catalyst is less than 50% of the amount of torque required to disperse the solid feedstock comprising lignin into the slurry liquid under the same conditions, prior to the application of the mechanical forces.

The amount of torque is the total amount of energy applied to the solid-slurry liquid mixture to disperse the solid into the slurry liquid. The amount of torque can be determined by the area under the curve of the line of the torque applied at a given point in time, t, corresponding to the point at which the solid is considered dispersed into the slurry liquid. A solid is considered dispersed into the slurry liquid when the numeral average of the percent of dry matter content of a statistically valid number of aliquots of the slurry liquid is within 2.5% of the percent of the total dry matter content in the slurry liquid.

The viscosity of the slurry comprised of lignin, measured at 25° C., a shear rate of 10 $s^{-1}$, of the mechanically dispersed solid feedstock comprising lignin dispersed in the slurry liquid content should be less than the viscosity of a slurry of the solid feedstock comprised of lignin dispersed in the slurry liquid prior to mechanical treatment; when measured under the same conditions (e.g. dry matter content).

After producing the slurry comprised of lignin, the slurry comprised of lignin may be maintained by way of mechanical agitation.

Another strategy for creating the slurry comprised of lignin where the lignin conversion is not co-sited with the pretreatment or fermentation of the ligno-cellulosic biomass (10) is to expose the solid feedstock comprising lignin in a slurry liquid, preferably water, to a vacuum or pressure less than atmospheric pressure, with less than 0.8 bar being preferred, with less than 0.7 bar being more preferred, less than 0.4 bar being even more preferred with less than 0.2 bar being the most preferred. The feedstock comprising lignin will rapidly expand into small particles, disassociate, and disperse. In this way, high shear mixing and/or high shear forces are avoided with higher concentrations possible. It is preferred to have at least some mechanical agitation occurring simultaneously with the vacuum step so as to more rapidly disperse the particles. The Slurry Creation Experimental Section and FIG. 5 quantitatively show the advantage of using vacuum on the solid feedstock comprising lignin prior to increasing the pressure on the slurry. The vacuum may be applied simultaneously with shear and agitation, through a conveying screw. The minimum time for the vacuum to remain applied is the time sufficient to disperse the particles to greater than 50% of the theoretical dispersion at 25° C., with greater than 75% dispersion at 25° C. more preferred and greater than 90% dispersion at 25° C. the most preferred. It is preferred that the solid feedstock comprising lignin be surrounded or encompassed by a slurry liquid for full effectiveness of the vacuum.

In a preferred embodiment this slurry liquid is water. In another embodiment, this slurry liquid comprises a hydrogen donor. 100% dispersion at 25° C. is the theoretical dispersion. The amount of dispersion is determined by measuring the amount of solids in a sample after 2 minutes of settling. If there were 16 gms of solid in 84 gms of liquid, the dry matter content at 100% dispersion would be 16%. At 50% of the theoretical dispersion, the dry matter content of the sample after 2 minutes of settling would be 8%.

A final strategy for creating the slurry comprised of lignin where the lignin conversion is not co-sited with the pretreatment or fermentation of the ligno-cellulosic biomass (10) is to expose the solid feedstock comprising lignin in a slurry liquid, preferably water, to high shear such as that found in a blender, which over time will also disperse the particles of the feedstock comprising lignin throughout the slurry. In another embodiment, the slurry liquid is a hydrogen donor.

In most instances the slurry liquid will be water or water in combination with at least one hydrogen donor. The ratio amount of the weight of the water of the slurry liquid to the dry weight of the lignin feedstock is preferably in the range of 0.3 to 9, with 0.5 to 9 more preferred, with 1 to 9 even more preferred with 2 to 9 another preferred ratio and 3 to 5 an even more preferred ratio.

SLURRY CREATION EXPERIMENTS

Experiments were conducted for evaluating slurry preparation under vacuum treatment in comparison with slurry preparation under standard mechanical agitation.

Slurry Creation Experiment 1

An amount of 450 g of lignin-rich composition, having a dry matter of 53%, was inserted into a 3 liter round bottom flask with 1050 g of water, to reach a theoretical concentration of 16% of dry matter of lignin-rich composition in the mixture. No mechanical mixing was applied.

The flask had a dimension of approximately 16 cm and was equipped with a stirrer with a dimension of approximately 6 cm.

The flask was sealed and vacuum of 29.8 mmHg was applied for 5 minutes and removed. After 2 minutes of sedimentation time, a first sampling of the slurry comprised of lignin was extracted.

Mechanical agitation was applied to the slurry comprised of lignin at atmospheric pressure for 1 minute, then mechanical agitation was stopped and after 2 minutes of sedimentation time a sampling was extracted. The mechanical agitation procedure was repeated further for 5, 10, 30, and 60 minutes of agitation time and samplings were extracted after a sedimentation time of 2 minutes each time.

No chunks were present at the bottom of the flask and the slurry comprised of lignin appeared to be homogeneously mixed.

Slurry Creation Experiment 2

A control experiment was realized by inserting an amount of 450 g of lignin-rich composition, having a dry matter of 53%, into a 3 liter round bottom flask with 1050 g of water, to reach a theoretical concentration of 16% of dry matter of lignin-rich composition in the mixture.

The flask and mechanical stirrer were the same as in the experiment conducted with vacuum. The slurry comprised of lignin was subjected only to mechanical agitation, and samplings were extracted after 5, 1, 5, 10, 30, 60 minutes of agitation. Before each sampling, the mechanical agitation was stopped for 2 minutes of sedimentation time.

A relevant amount of chunks were present at the bottom of the flask and the slurry comprised of lignin appeared to be inhomogeneous.

The mechanical agitation was obtained by stirring the slurry comprised of lignin at 250 rpm in both the experiments.

Concentration of dry matter of the lignin-rich composition was determined by drying samples in an oven at 105° C. for 15 hours.

Figure 5:
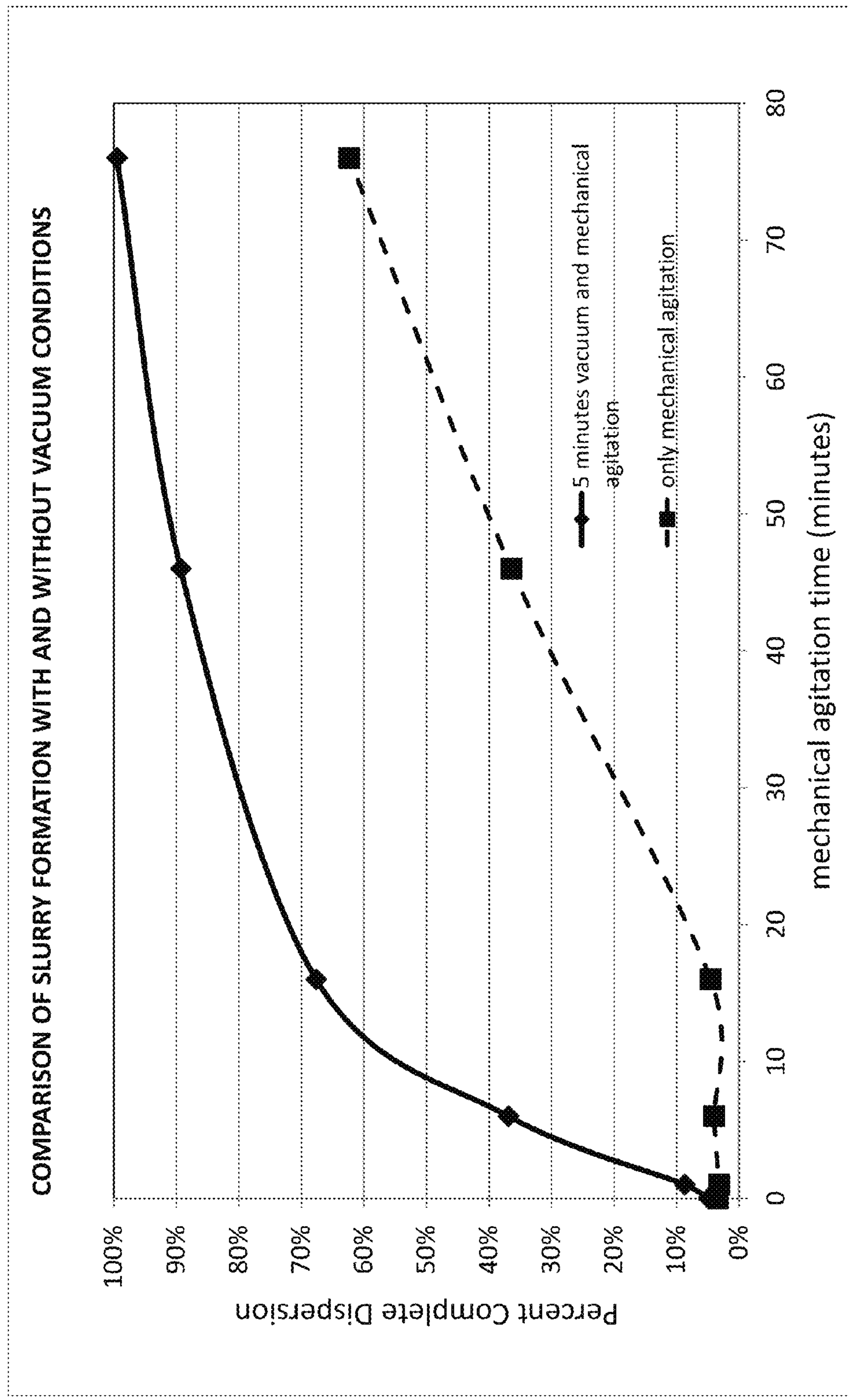
FIG. 5 shows the effect of mixing type and vacuum upon the final dispersed concentration versus time.
Figure 6:
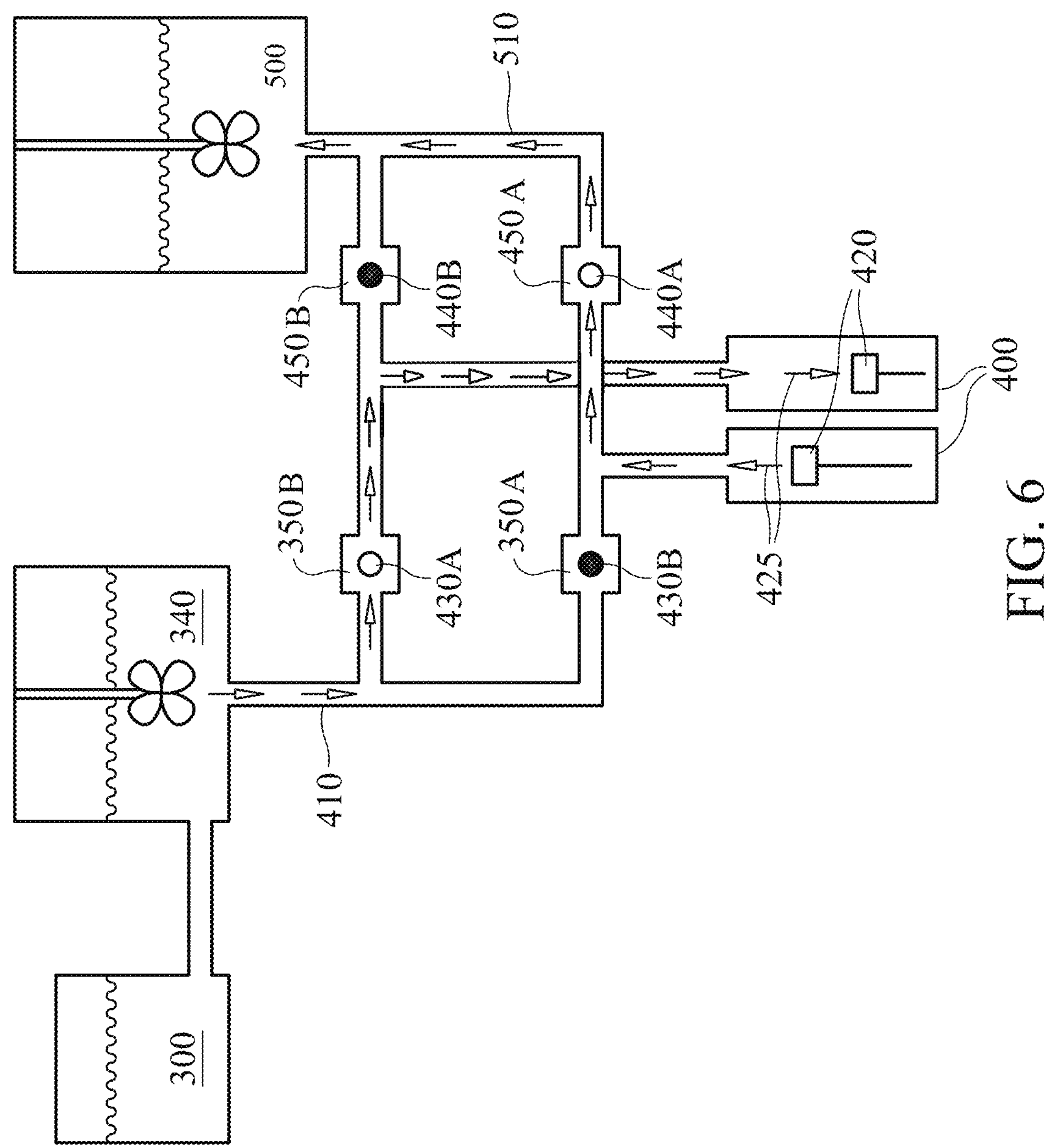
FIG. 6 shows the schematic of piston pumps and valves used for charging a slurry comprised of lignin to a lignin conversion reactor.
Figure 7:
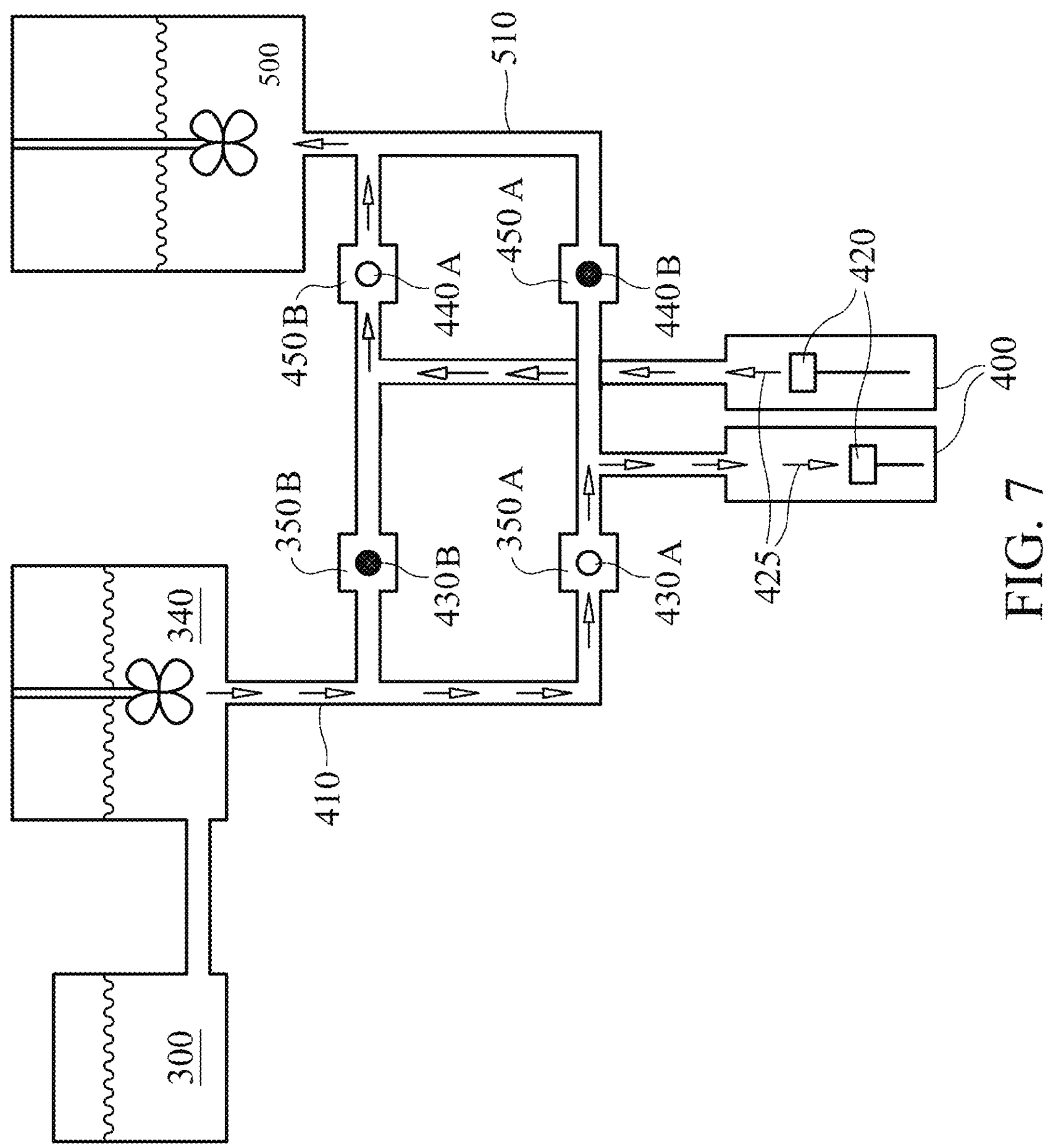
FIG. 7 shows the schematic of piston pumps and valves used for charging a slurry comprised of lignin to a lignin conversion reactor.
Figure 8:
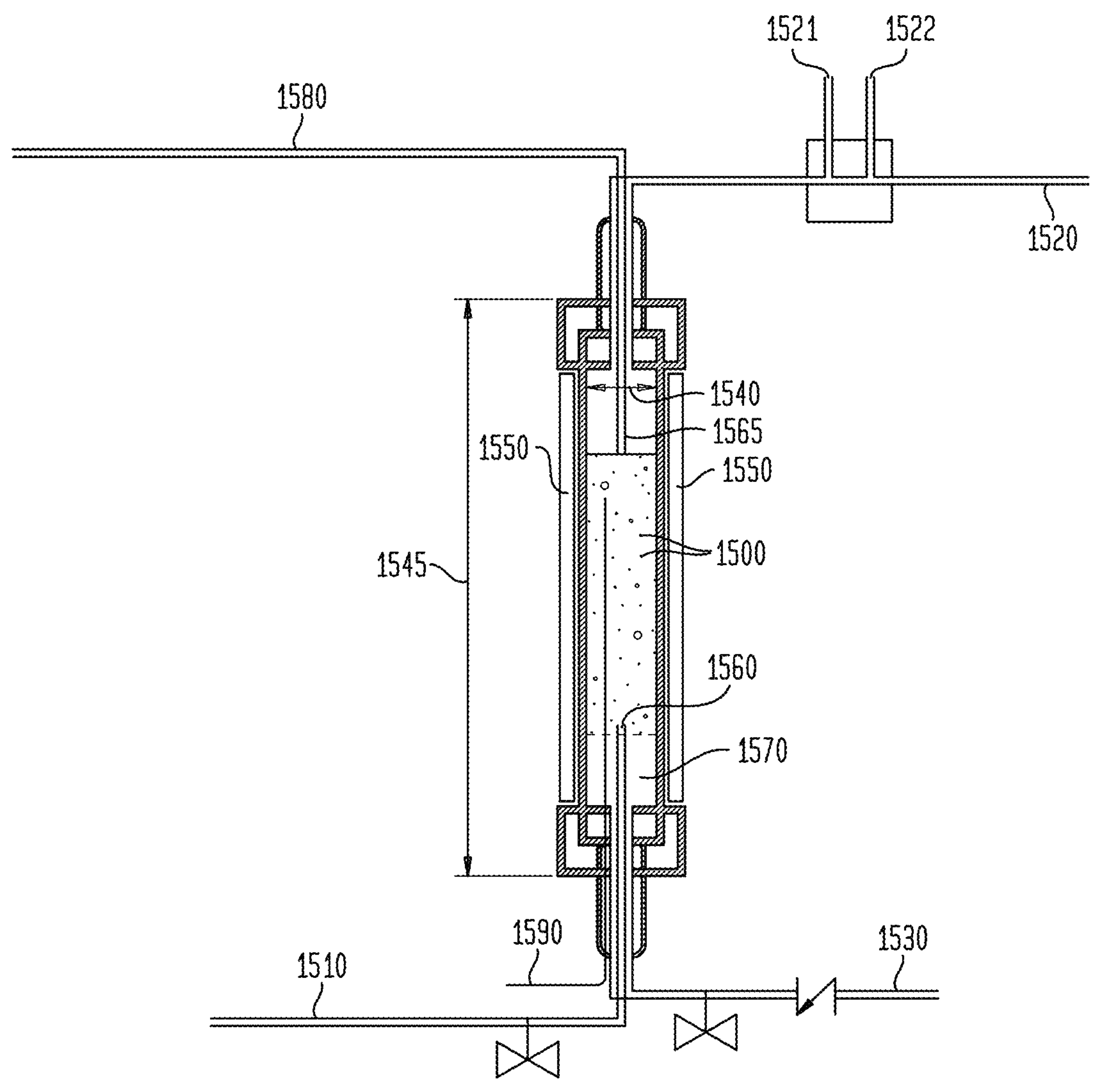
FIG. 8 shows the schematic of a bubble column.

FIG. 5 reports the graph of percent complete dispersion of the lignin-rich composition in the slurry comprised of lignin. The percent complete dispersion is the concentration of dry matter of lignin-rich composition in the slurry comprised of lignin normalized with respect to the theoretical concentration.

The experiment demonstrates that by applying a vacuum the time needed to obtain a full dispersion of the lignin-rich composition in the slurry comprised of lignin is strongly reduced, thereby enabling mixing energy savings, time savings and slurry tank volume reduction.

Slurry Pressurizing and Transport

After the slurry comprised of lignin is created it must be brought to a pressure slightly greater than the lignin conversion reactor pressure plus the pressure from the slurry pump exit to the lignin conversion reactor (500), so that the slurry can be charged into the lignin conversion reactor (500).

The slurry comprised of lignin can be pressurized using a slurry pump (400). For the purposes of this specification the term slurry pump (400) is meant to refer to any pump which can reach the desired pressures, such as a piston pump and/or a syringe pump. A multi-stage centrifugal pump may also reach the required pressures. The slurry pump (400), which is depicted as a piston pump used in the experiments will have an inlet valve (350). The inlet valve position can span the range from fully open to fully closed. Therefore, the inlet valve position can be selected from the group consisting of open, closed and at least partially open, wherein open means fully open (the restrictions across the valve as measured by pressure drop are the minimum possible), closed means fully closed so that no liquid or gas can pass through the valve, and at least partially open means the valve is not fully closed and not fully open, but somewhere in between fully closed and fully open. The slurry pump (400) will have an outlet valve (450). The outlet valve can be present in an outlet valve position selected from the group consisting of open, closed and at least partially open, with open, closed and at least partially open having the same meanings as for the inlet valve position.

The slurry pump (400) will further comprise a piston (420) and a piston chamber (425). The piston (420) forms a seal inside and against the piston chamber (425) to form a pump cavity. The size of the cavity depends upon where the piston (420) is within the piston chamber (425).

The slurry comprised of lignin is passed through the inlet valve (350) which is in the inlet valve position of at least partially open or open (430A) into the pump cavity formed by withdrawing at least a portion of the piston (420) from the piston chamber (425). During this inlet step, the outlet valve (450) is in the closed outlet valve position (440B). The pump cavity will be at an inlet pump cavity pressure. After an amount of slurry comprised of lignin enters the pump cavity, the inlet valve position is changed to closed (430B), or in other words, the inlet valve is closed. A force is then placed on or applied to the piston (420) in the piston chamber (425) until the pressure of the slurry comprised of lignin reaches the discharge pressure which is greater than the reactor operating pressure, also known as the lignin conversion reactor pressure or deoxygenation pressure. The reactor operates in the ranges of 80 to 245 bar, 80 to 210 bar, 90 to 210 bar and 90 to 175 bar. Therefore the discharge pressure of the pump should also be in the above ranges of 80 to 245 bar, 80 to 210 bar, 90 to 210 bar and 90 to 175 bar, but greater than the lignin conversion pressure. It should also be noted for the purposes of this specification that the terms lignin conversion vessel and lignin conversion reactor are interchangeable.

At least a portion of the slurry comprised of lignin is discharged from the pump cavity by opening the outlet valve (450), also known as changing the outlet valve position to a position selected from the group consisting of at least partially open and open. The piston (420) is further forced into the pump body to reduce the volume of the pump cavity and push at least a portion of the slurry comprised of lignin through the outlet valve (450). The outlet valve (450) is connected to the lignin conversion reactor (500) by tubing, piping or other connection. By connected to the lignin conversion reactor it is meant that material from the pump cavity can flow through the outlet valve and into the lignin conversion reactor (500) generally through a pipe, a tube or through a series of connected pipes or tubes. In one embodiment there may be a plurality of additional valves between the outlet valve and the lignin conversion reactor (500), such as a valve for isolating the lignin conversion reactor (500).

In order for the process to run in a continuous manner it is not necessary that the slurry comprised of lignin is continuously introduced to the lignin conversion reactor (500). For example, when only one piston pump is used, the slurry comprised of lignin is introduced into the lignin conversion reactor (500) in steady aliquots or pulses. Thus there are moments when there is no product entering the lignin conversion reactor. But, over time, the mass introduced into the lignin conversion reactor equals the mass removed from the lignin conversion reactor. One distinguishing feature between a continuous and a batch process is that, in a continuous process, the reaction is occurring or progressing at the same time that either the slurry comprised of lignin is introduced into the lignin conversion reactor (500) and/or the lignin conversion products are removed from the lignin conversion reactor. Another way to state this is that the conversion (e.g. deoxygenating, or hydrogenating) in the lignin conversion reactor occurs while simultaneously, or at the same time, removing at least a portion of the lignin conversion reactor contents from the lignin conversion reactor (500). Such removal is done in a continuous manner which includes an aliquot or pulse removal.

The previous art proposes the use of piston pumps or syringe pumps for high pressure reactor charging. However, the consensus of the art is to use check valves. This simple elegant approach has been used for years. However, as discovered by the inventors, check valves and other valve configurations will not work with a slurry comprised of lignin. The inventors consulted multiple pump and valve experts and evaluated the myriad of solutions proposed by the experts, none of which allowed the slurry comprised of lignin to be continuously charged to the lignin conversion reactor. A pressure could not be maintained or could not be maintained for long. The observations indicated that the tough, fibrous nature of lignin allows the lignin from the slurry comprised of lignin to get stuck in the valve seats and build up in areas of low flow or high impaction causing the valves to plug.

What was discovered is that a more complicated valving system worked. It was discovered that the industry standard and use of a simple check valve had to be replaced with a valve having a position that could be controlled and that the valve should provide unrestricted and unobstructed flow of the slurry comprising lignin through the valve or its flow path. By unrestricted flow it is meant that the flow of the slurry comprising lignin through the valve (flow path) does not change directions, such as in a bend, and does not increase in linear velocity, such as in a narrowing of the flow path. By unobstructed flow it is meant that the flow path does not contain any additional elements, such as the insert body of a butterfly valve, in the path of the slurry flow such that the slurry will have to flow around or strike the additional element when the valve is in the fully open position. Further, the flow path does not contain additional dead zones, such as the seat groove of a gate valve. Dead zones, such as the seat groove of a gate valve will fill with slurry when the valve is open and, when the valve is closed, the gate will compress the slurry into the groove which will allow for accumulation and compression of the slurry comprised of lignin in the groove. In this instance, over time the valve will not seat or seal, and will fail to hold pressure.

By way of example, but not limitation, a valve that provides for unrestricted and unobstructed flow of the slurry comprising lignin may include a ball valve, a full port ball valve or a full port fixed ball valve. In contrast, traditional valves such as most globe valves, most angle valves, most diaphragm valves, most butterfly valves and most check valves restrict and/or obstruct the flow of the slurry comprised of lignin and will cause the lignin from the slurry comprised of lignin to build up in areas of low flow or high impaction causing the valves to eventually plug or not seat or seal, and fail to hold pressure. (Examples of such valves are described in Chemical Engineers' Handbook, Fifth Edition, Perry & Chilton, p 6-54 through 6-57, 1973). In practice, this build up of lignin from the slurry comprised of lignin may occur quite rapidly, in some cases so rapidly that no amount of the slurry comprised of lignin will be charged through the inlet valve and into the pump cavity. (See Slurry Pumping Experiment 1).

By removing the check valve, the system was no longer automatic within the valve but needed special additional controls to turn each valve on and off in a synchronized manner. Therefore, in direct opposite of the prior art, and what the pump and valve experts proposed to the inventors on many occasions, the process only functioned when the inlet valve (350) and the outlet valve (450) were not check valves, but valves that provide for unrestricted and unobstructed flow. (A check valve being a valve which prevents the reversal of flow). It is preferable that the pressurization process, discharge and ultimate charge into the reactor be void of any check valves in the path of slurry flow. Alternatively, the slurry does not flow through a check valve into the slurry pump (400) to enter the reactor.

Different embodiments are available. For example there could be a plurality of slurry pumps comprising at least two piston pumps. Where there are two piston pumps each piston pump may have its own inlet valve and its own outlet valve (e.g. the first piston pump has a first inlet valve (350A) and a first outlet valve (450A) while the second piston pump has a second inlet valve (350B) and a second outlet valve (450B)). The plurality of slurry pumps can be in a parallel configuration. It is possible for two piston pumps in a parallel configuration to share the same inlet valve (350) and/or outlet valve (450). Another configuration is where the inlet valve (350) and outlet valve (450) are the same valve.

Eventually at least a portion of the slurry comprising lignin, a portion of which is in a solid form, is introduced into the lignin conversion reactor (500). The lignin conversion reactor will have a lignin conversion pressure and lignin conversion temperature. The lignin conversion pressure will be at least slightly less than the slurry pump discharge pressure which is at least the amount of pressure drop from the slurry pump (400) to the lignin conversion reactor inlet. Generally, the slurry pump discharge pressure will be greater than the lignin conversion pressure, with the slurry pump discharge pressure being greater than the lignin conversion reactor pressure plus the absolute amount of pressure drop in the process from the slurry pump discharge to the lignin conversion reactor (500).

SLURRY PUMPING EXPERIMENTS

Experiments were conducted for charging a slurry comprised of lignin to a pressurized lignin conversion reactor. The following procedures were applied to all the experiments, unless differently specified.

De-ionized water was added to a lignin-rich composition obtained from the pretreatment of ligno-cellulosic biomass to obtain a slurry comprised of lignin having a dry matter content of 20 weight percent of the mass of the slurry. The mixture was inserted into a blender (Waring Blender, model HGBSSSS6) and thoroughly mixed intermittently for one to two minutes to reach a homogeneous slurry. The homogeneity of the slurry was evaluated by eye. The slurry was inserted into a mix tank (340) with constant agitation. The mix tank (340) was a stainless steel, dish bottom tank with a volume of approximately 1 L containing a standard laboratory paddle mixer and a bottom discharge port connected to a Chandler Quizix QX dual syringe pump having two pump cavities. Inlet valves (350) were inserted between the mix tank (340) and the two pump cavities of the Chandler Quizix QX dual syringe pump. The Chandler Quizix QX dual syringe pump was connected by tubing to a Parr 4575 reactor equipped with a dual 45° pitched turbine blade, cooling coil, separate gas and slurry feed ports and a discharge dip tube (610). Outlet valves (450) were inserted between the two pump cavities of the Chandler Quizix QX dual syringe pump and the Parr reactor. Between 200 and 400 scfh of hydrogen at a temperature of 20° C. was inserted into the Parr reactor to reach a pressure of 48.3 bar. The Parr reactor was heated to a temperature corresponding to 90% of the reaction temperature and a continuous flow of Hydrogen was started into the Parr reactor. Final temperature and pressure in the Parr reactor varied between 275-325° C. and 100 and 175 bar. The pressure was measured by means of a pressure transducer (Ashcroft Type 62) connected to the Parr reactor.

The slurry comprised of lignin was passed from the mix tank (340) into the first of the two pump cavities of the Chandler Quizix QX dual syringe pump by changing the inlet valve position of the first inlet valve (350A) corresponding to the first pump cavity to the open position (430A) by means of an actuator. After the slurry comprised of lignin reached the first pump cavity, the first inlet valve (350A) corresponding to the first pump cavity was changed to the closed inlet valve position (430B) by means of an actuator. After the first inlet valve (350A) corresponding to the first pump cavity was closed, the slurry comprised of lignin was passed from the mix tank (340) into the second of the two pump cavities of the Chandler Quizix QX dual syringe pump by changing the inlet valve position of the second inlet valve (350B) corresponding to the second pump cavity to the open position (430A) by means of an actuator.

After the first inlet valve (350A) corresponding to the first pump cavity was closed (430B), the Chandler Quizix QX dual syringe pump pressurized the slurry comprised of lignin in the first pump cavity to a pressure greater than that of the Parr reactor. While the slurry comprised of lignin in the first pump cavity was being pressurized both the first inlet valve (350A) and the first outlet valve (450A) were closed. After the slurry comprised of lignin in the first pump cavity was pressurized to a pressure greater than that of the Parr reactor, the first outlet valve (450A) corresponding to the first pump cavity was changed to the open position (440A) by means of an actuator, allowing the pressurized slurry comprised of lignin in the first pump cavity to be charged to the Parr reactor.

After the first outlet valve (450A) corresponding to the first pump cavity was opened, the second inlet valve (350B) corresponding to the second pump cavity was changed to the closed position (430B) by means of an actuator. After the second inlet valve (350B) corresponding to the second pump cavity was closed (430B), the Chandler Quizix QX dual syringe pump pressurized the slurry comprised of lignin in the second pump cavity to a pressure greater than that of the Parr reactor. While the slurry comprised of lignin in the second pump cavity was being pressurized both the second inlet valve (350B) and the second outlet valve (450B) were closed. The pressure of the Parr reactor is the deoxygenation pressure and can range from 90 to 175 bar. After the slurry comprised of lignin in the second pump cavity was pressurized to a pressure greater than that of the Parr reactor, the first outlet valve (450A) corresponding to the first pump cavity was changed to the closed position (440B) by means of an actuator. After the first outlet valve (450A) corresponding to the first pump cavity was closed, the second outlet valve (450B) corresponding to the second pump cavity was changed to the open (440A) position by means of an actuator, allowing the pressurized slurry comprised of lignin in the second pump cavity to be charged to the Parr reactor.

After the second outlet valve (450B) corresponding to the second pump cavity was opened, the first inlet valve (350A) corresponding to the first pump cavity was changed to the open position (430A) by means of an actuator, allowing additional slurry comprised of lignin from the mix tank (340) into the first pump cavity to be pressurized and subsequently charged to the Parr reactor.

Slurry Pumping Experiments 1 and 2

For Slurry Pumping Experiments 1 and 2, the inlet valves and outlet valves were small orifice, rising stem valves from Vindum Engineering, Model No. CV-505-SS. These valves were recommended by an expert in the field of slurry pumping, and were represented as sufficient for charging a slurry comprised of lignin to a pressurized reactor.

For Experiment 1, when the inlet valve corresponding to the first pump cavity was changed to the open position, it immediately plugged with solid lignin from the slurry comprised of lignin. No amount of the slurry comprised of lignin reached the first pump cavity, the outlet valve corresponding to the first pump cavity, or the Parr reactor.

For Experiment 2, an expert in the field of slurry pumping recommended pressurizing the mix tank (340) to between 2.5 to 3 bar to assist with charging the slurry comprised of lignin through the inlet valves into the pump cavities. The expert represented that pressurizing the mix tank (340) would allow the slurry comprised of lignin to pass through the inlet valves into the pump cavities without plugging the inlet valves. When the inlet valve corresponding to the first pump cavity was changed to the open position, it immediately plugged with solid lignin from the slurry comprised of lignin without any amount of the slurry comprised of lignin reaching the first pump cavity, the outlet valves, or the Parr reactor.

Slurry Pumping Experiments 3 and 4

For Experiments 3 and 4, an expert in the field of slurry pumping recommended that the inlet valves and outlet valves be replaced with Swagelock Bellows Seal Valves, Model No. SS-HBS6-C. The inlet valves and outlet valves of Experiments 3 and 4 had a larger orifice than those of Experiments 1 and 2, and the expert represented that these larger orifices would allow the slurry comprised of lignin to pass through the inlet valves into the pump cavities without plugging the inlet valves.

For Experiment 3, when the inlet valve corresponding to the first pump cavity was changed to the open position, it allowed a portion of the slurry comprised of lignin into the first pump cavity to be charged to the Parr reactor. However, after a time of between 15 and 20 minutes the inlet valves again plugged with solid lignin from the slurry comprised of lignin.

For Experiment 4, an expert in the field of slurry pumping recommended pressurizing the mix tank (340) to between 2.5 and 3 bar to assist with charging the slurry comprised of lignin through the inlet valves into the pump cavities. The expert again represented that pressurizing the mix tank (340) would allow the slurry comprised of lignin to pass through the inlet valves into the pump cavities without plugging the inlet valves. When the inlet valve corresponding to the first pump cavity was changed to the open position, it allowed a portion of the slurry comprised of lignin into the first pump cavity to be charged to the Parr 4575 reactor. However, after a time of between 25 and 30 minutes the inlet valves again plugged with solid lignin from the slurry comprised of lignin.

Slurry Pumping Experiments 5 and 6

For Experiment 5, the inventors decided to replace the inlet valves with Swagelok 60 Series 3 piece Ball Valves, Model No. SS-62TS6. The outlet valves were the same Swagelock Bellows Seal Valves used in Experiments 3 and 4. When the inlet valve corresponding to the first pump cavity was changed to the open position, it allowed a portion of the slurry comprised of lignin into the first pump cavity, which was subsequently passed through the outlet valve corresponding to the first pump cavity and charged to the Parr reactor. The process was run for a period of approximately two days, at which time the outlet valves became plugged with solid lignin from the slurry comprised of lignin.

For Experiment 6, the inlet valves were the same Swagelok 60 Series 3 piece Ball Valves as those used in Experiment 5, however, the inventors decided to replace the outlet valves with Swagelok 60 Series 3 piece Ball Valves, Model No. SS-62TS6. When the inlet valve corresponding to the first pump cavity was changed to the open position, it allowed a portion of the slurry comprised of lignin into the first pump cavity, which was subsequently passed through the outlet valve corresponding to the first pump cavity and charged to the Parr reactor. The pump was then able to continuously charge the slurry comprised of lignin into the Parr reactor without plugging the inlet valves or outlet valves. It was not necessary to pressurize the mix tank (340) in order to charge the reactor.

Char Prevention

One of the difficulties in any continuous lignin conversion process is avoiding the formation of char. Char formation results in decreased yields of lignin conversion products, and disrupts the continuous nature of the lignin conversion process, as the lignin conversion process must be shut down and the char removed from the lignin conversion reactor before continuing the process.

The Inventors discovered that, to avoid char, the deoxygenation, which is the exposure of the lignin to hydrogen as either $H_2$ gas or via a hydrogen donor, occurs at a lignin conversion temperature and a lignin conversion pressure, wherein the lignin conversion temperature is in the range of greater than the boiling point of the liquid composition in the reactor at atmospheric pressure, and less than the critical temperature of the liquid composition, with the lignin conversion pressure being greater than the bubble pressure of the liquid composition in the reactor at the lignin conversion temperature, subject to the condition that the lignin conversion pressure is selected so as to avoid the formation of char.

The liquid composition of the reactor is the composition of the liquid components that are added to the vessel. For example, in one embodiment, the liquid composition is almost pure water with dissolved species. In the case of pure water the hydrogen would come from added hydrogen gas. In the case of pure water or substantially pure water, the bubble pressure is the vapor pressure of the water at the lignin conversion temperature. In another embodiment, the liquid composition could comprise water and a hydrogen donor. This liquid composition has its own bubble pressure and critical temperature forming the lower and upper boundary of the temperature range, subject to the additional condition that the lignin conversion pressure be selected so as to avoid char formation after two residence cycles, which can be visually verified by opening the reactor after two residence cycles and observing the presence or absence of char—a dark residue coating the reactor. The reactor will also be void of any liquid.

What has been discovered is that the lignin conversion pressure is also a function of the amount of gas exiting the reactor. The higher the amount of gas used, such as in hydrogen gas or nitrogen, the greater the pressure required. In the instance of a hydrogen donor, less gas is used and thus a lower lignin conversion pressure is needed to prevent char.

The proper lower lignin conversion pressure can be easily empirically established as follows. One can determine the liquid composition charged to the reactor. In most cases it will be water from the slurry and whatever hydrogen donor compounds, if any, are used. The design will include a flow rate for the gas exiting the reactor. While the calculations can be done manually, a commercial simulation package can be used to determine the vapor liquid equilibrium conditions (bubble pressure) of the liquid mixture. This is demonstrated in Table 2 which is the "calculated reactor pressure for liquid water" using water as the liquid. As can be seen by the table, the theoretical calculations are a close approximation, but in the case of water, the actual pressure was still greater than the calculated amount based upon the pure components. Once the approximation is determined, the reaction can be conducted for two residence cycles, the vessel opened and examined for char. If there is char, the reaction pressure is increased until there is no char and thus subject to the condition that no char is formed after two residence cycles.

A residence cycle is the amount of time to turn over the reactor contents. If the residence volume is 4 L in the vessel and the vessel is being charged at a volumetric flow rate at operating conditions of 1 L/hr, the residence cycle is 4 hours and 2 residence cycles is 8 hours. At 2 L/hr, the residence cycle is 2 hrs and 2 residence cycles is 4 hours.

As demonstrated above the lignin conversion process should occur at a lignin conversion temperature, where the lignin conversion temperature is in the range of greater than the boiling point of the slurry liquid at atmospheric pressure, and less than the critical temperature of the slurry liquid, subject to the condition that the lignin conversion pressure is greater than the bubble pressure of the slurry liquid at the lignin conversion temperature and the lignin conversion pressure is selected so as to avoid the formation of char.

To avoid char formation, the lignin conversion pressure should be selected so that the lignin conversion pressure is greater than the bubble pressure of the slurry liquid at the lignin conversion temperature. Bubble pressure is the sum of the partial vapor pressures of all components in the lignin conversion reactor.

When the slurry liquid is comprised of water, the lignin conversion process should occur at a lignin conversion temperature below the critical temperature of water.

Generally, the lignin conversion process will occur at a lignin conversion temperature in the range of 190° C. to 370° C. The lignin conversion temperature range is preferably selected from the group consisting of 190° C. to 370° C., 210° C. to 370° C., 220° C. to 360° C., 240° C. to 360° C., 250° C. to 360° C., 280° C. to 360° C., 290° C. to 350° C., and 300° C. to 330° C.

Where the slurry liquid is comprised of a hydrogen donor, the lignin conversion process may occur at a lignin conversion temperature in the range of 190° C. to 350° C. with 200° C. to 310° C. being more preferred, 210° C. to 300° C. being even more preferred, and 210° C. to 280° C. being most preferred.

The hydrogen donor may also be introduced into the lignin conversion reactor separately from the liquid slurry. The hydrogen donor may also come from the carbohydrate conversion step, thus the ligno-cellulosic biomass is generating its own hydrogen for use in the process. In such a process, the hydrogen donor, such as ethylene glycol, could be manufactured in the carbohydrate conversion step of FIG. 3 and passed to the liquid slurry and introduced into the lignin conversion reactor via stream 325.

In order to avoid char it is also important to control the lignin conversion pressure as described above. The lignin conversion pressure is in a range preferably selected from the group consisting of 70 bar to 300 bar, 80 bar to 245 bar, 82 bar to 242 bar, 82 bar to 210 bar, 90 bar to 207 bar and 90 bar to 172 bar.

The continuous lignin conversion in the presence of carbohydrates should occur at a lignin conversion pressure higher than the theoretical equilibrium vapor pressure of water at the lignin conversion temperature. It was directly observed that char was formed when the lignin conversion pressure was even greater than the calculated water vapor pressure at the lignin conversion temperature accounting for the exiting gas sweeping across the top of the liquid. No char was observed when the lignin conversion pressure was substantially higher than the calculated water vapor pressure at the lignin conversion temperature. What was discovered is that to avoid char formation in a continuous process it was necessary to maintain at least a portion of the reactor contents as a liquid, but to do so, required pressures much higher than expected or would have been predicted.

Char formation is not seen in batch reactor conditions because batch reactor conditions are always at theoretical equilibrium. When the exit sweeping gas is introduced in the continuous process, the equilibrium conditions no longer exist and the pressure required to keep at least some of the reactor contents as a liquid in the lignin conversion reactor is substantially higher than conventional wisdom or innovation would teach. While process simulations can be made to initially approximate the lignin conversion pressure at given conditions, the actual minimum lignin conversion pressure can be easily empirically established by increasing the pressure until no char is observed. Those practicing the invention are cautioned that the increase in pressure can be large depending upon the flow rates from the reactor.

Char Prevention Experiments

The following procedures were applied to all the experiments, unless differently specified.

De-ionized water was added to a lignin-rich composition obtained from the pretreatment of ligno-cellulosic biomass to obtain a slurry comprised of lignin having a dry matter content of 20 weight percent of the mass of the slurry. The mixture was inserted into a blender (Waring Blender, model HGBSSSS6) and thoroughly mixed intermittently for 10 min. to reach a homogenous slurry. The homogeneity of the slurry was evaluated by eye. The slurry was inserted into a mix tank with constant agitation. The mix tank was a stainless steel, dish bottom tank with a bottom discharge port connected to a Chandler Quizix QX dual syringe pump having two pump cavities. Inlet valves were inserted between the mix tank and the two pump cavities of the Chandler Quizix QX dual syringe pump. The Chandler Quizix QX dual syringe pump was connected by tubing to a Parr 4575 reactor equipped with a dual 45° pitched turbine blade, cooling coil, separate gas and slurry feed ports and a discharge dip tube. Outlet valves were inserted between the two pump cavities of the Chandler Quizix QX dual syringe pump and the Parr reactor.

Hydrogen at a temperature of 20° C. was inserted into the Parr reactor to reach a pressure of 48.3 bar. The Parr reactor was heated to a temperature corresponding to 90% of the reaction temperature and continuous flow of Hydrogen was started into the Parr reactor. The pressure was measured by means of a pressure transducer (Ashcroft Type 62) connected to the Parr reactor.

The slurry comprised of lignin was passed from the mix tank through the Chandler Quizix QX dual syringe pump and into the Parr reactor by opening and closing the inlet and outlet valves in a manner that allowed the slurry comprised of lignin to pass continuously into the Parr reactor.

Experiments were conducted according to the described procedure. Experimental parameters are reported in Table 1.

TABLE 1

EXPERIMENTAL PARAMETERS

| | | H2 | | Flow Rate | | Lignin-rich composition | Residence | Catalyst to Lignin-rich | Unreacted Lignin | % |
|---|---|---|---|---|---|---|---|---|---|---|
| Exp. No. | Temp (° C.) | Flow (sccm) | Press. (bar) | Slurry (mL/min) | Solids (g/min) | Concentration (wt %) | time (min) | composition ratio | (% of Theoretical) | Catalyst Loss |
| 1 | 340 | 150 | 156.1 | 2.8 | 0.42 | 15 | 53 | 0.50 | | |
| 2 | 340 | 500 | 173.4 | 5.6 | 0.84 | 15 | 26 | 2.60 | | |
| 3 | 340 | 500 | 173.4 | 2.8 | 0.42 | 15 | 51 | 1.25 | | |
| 4 | 305 | 100 | 122.4 | 3.8 | 0.19 | 5 | 45 | 0.25 | 3.1 | 13.3 |
| 5 | 325 | 100 | 166.5 | 3.8 | 0.19 | 5 | 42 | 0.25 | 0.2 | 1.7 |
| 6 | 305 | 800 | 122.4 | 3.8 | 0.19 | 5 | 45 | 2.00 | 0.6 | 1.3 |
| 7 | 325 | 100 | 166.5 | 2.3 | 0.12 | 5 | 70 | 0.25 | 0.3 | 1.1 |
| 8 | 305 | 100 | 122.4 | 3.8 | 0.57 | 15 | 45 | 2.00 | 20.8 | 18.4 |

Large amounts of char without liquid water was observed in the reaction products of experiments 1-3. No char and liquid water was observed in Experiments 4-8.

It is believed that it is necessary to have liquid present, such as water in the liquid phase, for the reaction to progress as opposed to decomposition.

What was discovered was that even though the reactor was operated at a total system (reactor) pressure well above the vapor pressure of water at the 340° C. (146.1 bar) vs. the gas pressure, there was still no water or solvent present.

TABLE 2

COMPARISON OF REACTOR CONDITIONS VS CHAR FORMATION

| Exp. No. | Temp. | Vapor pressure of pure water | Minimum calculated Reactor pressure for Liquid Water (bar) | Reactor Pressure | Char |
|---|---|---|---|---|---|
| 1 | 340 | 146.1 | 165.3 | 156.1 | Yes |
| 2 | 340 | 146.1 | 172.9 | 173.4 | Yes |
| 3 | 340 | 146.1 | 196.3 | 173.4 | Yes |
| 4 | 305 | 92.1 | 95.6 | 122.4 | No |
| 5 | 325 | 120.7 | 125.8 | 166.5 | No |
| 6 | 305 | 92.1 | 116.3 | 122.4 | No |
| 7 | 325 | 120.7 | 128.6 | 166.5 | No |
| 8 | 305 | 92.1 | 98.2 | 122.4 | No |

Catalyst Retention and Separation

Because the lignin conversion catalyst is present as free particles (625), and not a fixed bed, the lignin conversion catalyst needs separated from the lignin conversion products. The catalyst particles (625) can be separated from the liquid lignin conversion products after the liquid lignin conversion products are removed from the lignin conversion reactor (500) by filtering, settling, centrifuging, solid bowl centrifuging, cycloning or other processes known in the art. The separated catalyst is then either re-introduced into the lignin conversion reactor for further reactions, treated for replenishment and then reused, or discarded. These traditional methods are known.

It has been discovered that the free catalyst particles (625) can be separated from the lignin conversion products in situ, that is within the lignin conversion reactor (500) while the continuous catalytic conversion of the lignin feedstock to lignin conversion products is occurring. Thus, the lignin conversion products can be separated from the catalyst particles (625) during the continuous catalytic conversion of a lignin feedstock to lignin conversion products.

This separation is done by gravity settling, wherein the fluid linear velocity (meters/min) of the lignin conversion products (liquid and gas) leaving the lignin conversion reactor is less than the gravitational linear settling velocity of the catalyst particles (625) in the liquid/gas lignin conversion product stream exiting the reactor. Therefore, as long as the lignin conversion products being removed from the lignin conversion reactor are removed from the lignin conversion reactor at a linear velocity less than the settling velocity of the catalyst particles (625) and from a point higher (relative to gravity) than the liquid level in the reactor, catalyst particles will stay in the lignin conversion reactor.

The liquid level of the lignin conversion reactor is at the physical interface of the bulk liquid phase and bulk gas phase in the lignin conversion reactor (500). The bulk gas phase is a continuous gas phase which has a specific gravity which is less than the specific gravity of the bulk liquid phase. The bulk gas phase may have droplets of liquid in the bulk gas phase. Likewise, the bulk liquid phase is a continuous liquid phase and will have dissolved gases and gas bubbles.

The height relative to the liquid level at which the lignin conversion products are removed from the lignin conversion reactor is called the disengagement height. The disengagement height is greater than the catalysts particles travel height which is the height the catalyst particles (625) will reach when carried along with the lignin conversion products. Because the settling velocity of the catalyst particles is greater than the lignin conversion products removal velocity, the catalyst particles (625) will eventually drop back into the lignin conversion reactor (500) so long as the disengagement height in the settling zone as discussed below is large enough relative to the travel height so that at least a majority of the catalyst particles (625) do not reach the point at which the lignin conversion products are removed from the lignin conversion reactor.

Figure 4:
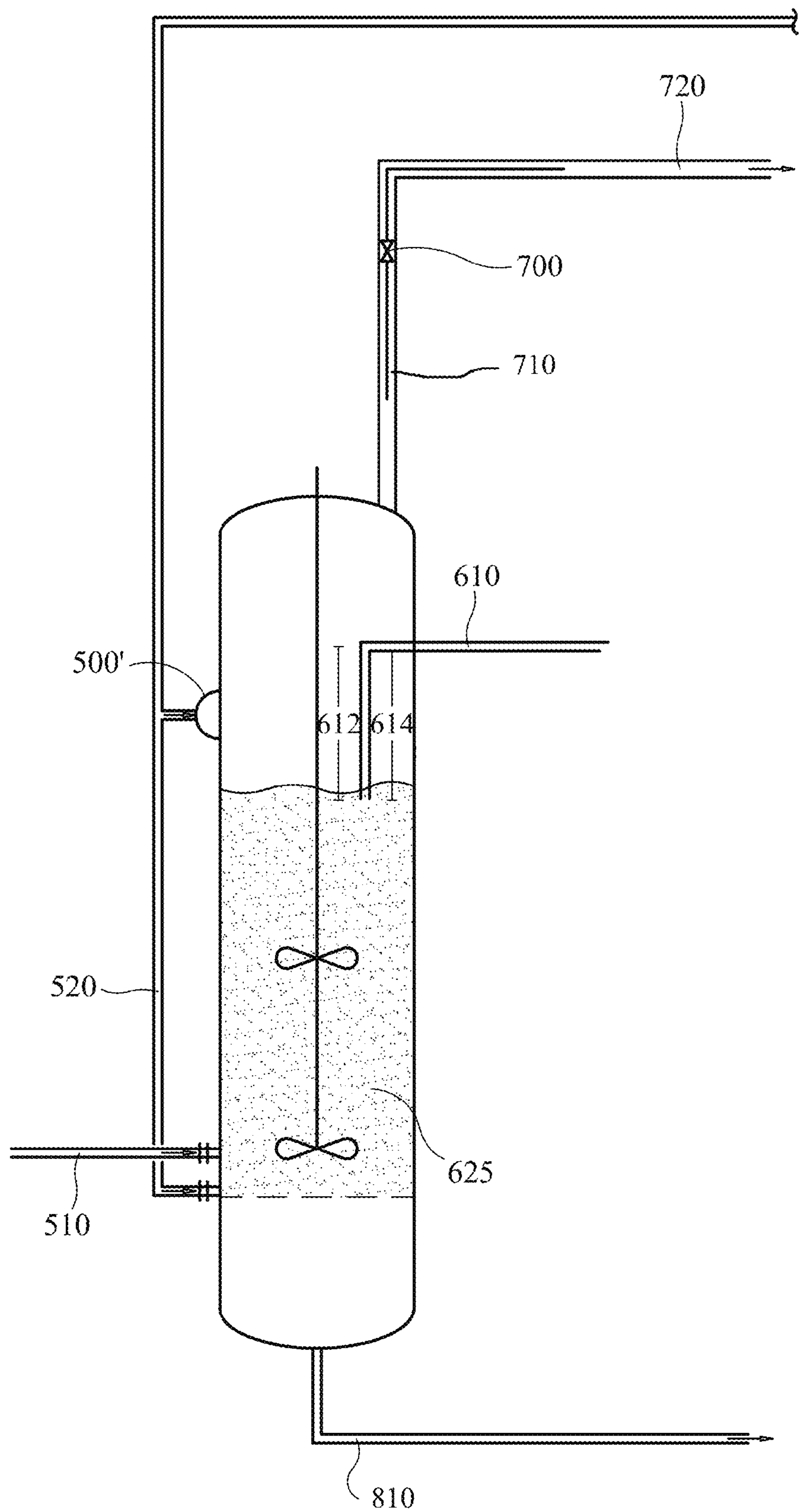
FIG. 4 shows an embodiment of a continuous stir tank reactor for the lignin conversion process.

In practice, so long as the settling velocity of the catalyst particles is substantially greater than the liquid lignin conversion products removal velocity, the disengagement height should be large enough so that at least a majority of the catalyst particles (625) never reach the point at which the liquid lignin conversion products are removed from the lignin conversion reactor. For example, where the liquid lignin conversion products are removed through an "L" shaped dip tube having a dip tube major length (612) and a dip tube minor length (614) as shown in FIG. 4, the disengagement point must be less than the dip tube minor length (614). If the dip tube minor length (614) is one meter, the settling velocity of the catalyst particles is 1.2 meters per second, and the liquid lignin conversion products removal velocity is 1 meter per second the liquid lignin conversion products will reach the disengagement height (which is also the dip tube minor length (614)) in one second. Because the catalyst particles (625) have a settling velocity which is 0.2 meters per second greater than the liquid lignin conversion products velocity, the catalyst particles (625) will travel up the dip tube (610) at a velocity which is 0.2 meters per second less (0.8 meters per second in this example) than the liquid lignin conversion products travel up the dip tube. As a result, when the liquid lignin conversion products reach the disengagement height (which is also the dip tube minor length (614)) of one meter after one second, the catalyst particles (625) will have only traveled 0.8 meters. In this manner, the catalyst particles never reach the disengagement height and will "settle" back into the lignin conversion reactor (500).

Conversely, if the settling velocity of the catalyst particles is less than the liquid lignin conversion products removal velocity, the catalyst particles (625) will reach or exceed the disengagement height and will be removed from the reactor. For instance, if the settling velocity of the catalyst particles is 0.8 meters per second and the liquid lignin conversion products removal velocity is 1 meter per second, the catalyst particles (625) will be travelling at a velocity at least equal to the liquid lignin conversion products. In this manner the catalyst particles will reach the disengagement height at least at the same time as the liquid lignin conversion products, and will thereby be removed from the lignin conversion reactor (500) through the dip tube (610).

In a preferred embodiment, the lignin conversion reactor will have an agitation zone and a settling zone, also known as a decantation zone. In the settling zone, the liquid phase of the reactor is exposed to less agitation than in the agitation zone. The settling zone can be created by use of a dip tube as discussed below. The internal of the dip tube sees very little agitation and is thus the settling zone in that embodiment. The settling zone can also be created by placing baffles above the agitator but below the liquid level to create a still spot. Another way is to have a separate reactor or vessel which does not have agitation. This configuration is described in the bubble column section. The lignin conversion products are removed from the settling zone at a lignin conversion products removal velocity. In order for more efficient removal of the catalyst, the lignin conversion products removal is subject to the condition that to reach the point in the lignin conversion reactor which is higher relative to gravity than the liquid level of the lignin conversion reactor, the lignin conversion products must leave the agitation zone and pass through a portion of the settling zone FIG. 4 demonstrates an embodiment of the principles. In this embodiment, the product is removed via a dip tube (610), where the lignin conversion products must exit up and out the dip tube. As the lignin conversion products travel up the tube, the first catalyst particles (625) travel with it. However, the first catalyst particle will have a terminal or settling velocity—that is the speed at which the particle drops through the liquid lignin conversion products of the reactor. If one observes catalyst particles (625) coming out the dip tube (610), it is a simple matter to enlarge the diameter of the dip tube to reduce the lignin conversion products velocity relative to gravity (slow down the speed) so that the conversion products travel up the tube relative to gravity at a speed less than the speed at which the first catalyst particles are dropping down the tube, thus keeping the catalyst in the reactor. If one wished to purge the catalyst, or add new catalyst so that the old catalyst could be removed, one would reduce the diameter of the tube (increasing the flow rate) and have catalyst particles (625) flow out of the lignin conversion reactor (500). The catalyst removal and replenishment can be done continuously so that a predetermined percentage of catalyst is removed and replenished on a continuous basis.

In practice, the catalyst particles (625) will vary in size and shape, each having a different settling velocity. Therefore, the preferred lignin conversion products removal velocity is less than the settling velocity of at least 75% by weight of the catalyst particles, with a lignin conversion products removal velocity less than the settling velocity of at least 85% by weight of the catalyst particles being more preferred, with a lignin conversion products removal velocity less than the settling velocity of at least 90% by weight of the catalyst particles being even more preferred, with a lignin conversion products removal velocity less than the settling velocity of at least 95% by weight of the catalyst particles being yet even more preferred, with a lignin conversion products removal velocity less than the settling velocity of 100% by weight of the catalyst particles being most preferred.

The "75% by weight of the catalyst particles" means that 75% by weight of the total amount of catalyst in the reactor remains in the reactor and 25% by weight of the total amount of the catalyst in the reactor is removed. Alternatively, the percent equals $$100*R/[R+X]$$

Where R is the weight of the catalyst remaining, X is the weight of the catalyst exited or removed from the reactor. The 100 is to make the number a percent.

One of ordinary skill can now easily see how a properly designed system could continually replenish catalyst—say add 5% by weight of new catalyst while removing 5% by weight. Thus, the catalyst is constantly being turned over.

CATALYST RETENTION EXPERIMENTS

Experiments were conducted for retaining catalyst in the reactor. The following procedures were applied to all the experiments, unless differently specified.

De-ionized water was added to a lignin-rich composition obtained from the pretreatment of ligno-cellulosic biomass to obtain a slurry comprised of lignin having a dry matter content of 20 weight percent of the mass of the slurry. The mixture was inserted into a blender (Waring Blender, model HGBSSSS6) and thoroughly mixed intermittently for 10 min. to reach a homogenous slurry. The homogeneity of the slurry was evaluated by eye. The slurry was inserted into a mix tank (340) with constant agitation. The mix tank (340) was a stainless steel, dish bottom tank with a bottom discharge port connected to a Chandler Quizix QX dual syringe pump having two pump cavities. Inlet valves (350) were inserted between the mix tank (340) and the two pump cavities of the Chandler Quizix QX dual syringe pump. The Chandler Quizix QX dual syringe pump was connected by tubing to a Parr 4575 reactor equipped with a dual 45° pitched turbine blade, cooling coil, separate gas and slurry feed ports and a stainless steel discharge dip tube (610) having an outside diameter of 0.25 inches and an inside diameter of 0.152 inches. Outlet valves were inserted between the two pump cavities of the Chandler Quizix QX dual syringe pump and the Parr reactor.

The lignin conversion reactor pressure was controlled by a Mity Mite Model 91 Back Pressure Regulator (BPR) positioned in the lignin conversion reactor discharge line between the Parr reactor and the products receiver. The lignin conversion pressure was measured by means of a pressure transducer (Ashcroft Type 62) connected to the Parr reactor.

The Parr reactor was charged with 150 mL of de-ionized water prior to beginning the experiments. The lignin conversion reactor pressure was increased to 48.3 bar by way of 20° C. hydrogen. The lignin conversion reactor was heated to 90% of the lignin conversion temperature prior to charging the slurry comprised of lignin to the lignin conversion reactor. After increasing the temperature to 90% of the lignin conversion temperature, additional de-ionized water was passed from the mix tank (340) through the Chandler Quizix QX dual syringe pump into the lignin conversion reactor (500) at a rate of 2.8 mL/min. Hydrogen flow was added to the lignin conversion reactor at a rate of 150 sccm. At this point, the temperature in the lignin conversion reactor was increased to 100% of the lignin conversion temperature, and the lignin conversion reactor pressure was adjusted via the BPR to the desired operating pressure as reflected in the experiments.

Slurry comprised of lignin was then charged to the reactor through the Chandler Quizix QX dual syringe pump at a rate of 2.8 mL/min. The slurry comprised of lignin was passed from the mix tank (340) through the Chandler Quizix QX dual syringe pump and into the Parr reactor by opening and closing the inlet valves (350) and outlet valves (450) in a manner that allowed the lignin slurry to pass continuously into the Parr reactor. The lignin conversion products were continuously removed from the lignin conversion reactor (500) via the dip tube (610) and cooled to approximately 35° C. before passing through the BPR. After passing through the BPR, the lignin conversion products were collected in a stainless steel products receiver fitted with a vent line to allow non-condensable gases from the lignin conversion reactor to separate from the liquid lignin conversion products.

The lignin conversion reactor was allowed to reach steady state conditions, and after four reactor residence cycles, the lignin conversion products were collected in the products receiver for approximately one additional reactor residence cycle. At this time, all feed streams to the lignin conversion reactor were stopped, and the lignin conversion reactor was isolated from the products receiver by way of an isolation valve. The lignin conversion reactor was cooled to approximately 30° C. and the pressure was reduced to atmospheric pressure by opening a vent valve.

The liquid lignin conversion products were mixed with an equal amount of methyl tertiary butyl ether (MTBE). This mixture was filtered through a Buchner funnel fitted with a Whatman #1 filter paper.

Catalyst Retention Experiment 1

For Experiment 1, sponge nickel catalyst was added directly to the slurry comprised of lignin resulting in a slurry comprised of 13.5 weight percent lignin on a dry basis and 7.0 weight percent sponge nickel catalyst on a dry basis. The sponge nickel catalyst had a particle size range of between 10 and 40 μm. The lignin conversion reactor was operated at 340° C. and 156.4 bar, which is approximately 10 bar above the vapor pressure of water at 340° C. At operating conditions, the average residence time of the slurry comprised of lignin was 53 minutes.

Surprisingly, after the experiment was stopped and the liquid lignin conversion products were filtered, very little catalyst was observed on the filter paper, and in one instance, no catalyst was observed at all. Where catalyst was observed on the filter paper, it was observed as fine particles of catalyst. When the Parr reactor was shut down and opened, it was surprisingly observed that nearly all of the catalyst remained in the lignin conversion reactor.

Catalyst Retention Experiment 2

For Experiment 2, 28 g on a dry basis of the sponge nickel catalyst was charged directly to the Parr reactor, along with the initial 150 mL of de-ionized water, prior to beginning the experiment. No amount of catalyst was added to the slurry comprised of lignin prior to charging the slurry comprised of lignin to the lignin conversion reactor. As a result, the slurry comprised of lignin contained 15 weight percent lignin on a dry basis. The lignin conversion reactor was operated at 340° C. and 173.4 bar, which is approximately 17 bar above the vapor pressure of water at 340° C. Hydrogen flow rate was increased to 500 sccm. Slurry feed rate and average residence time remained the same as in Experiment 1.

Surprisingly, after the experiment was stopped and the liquid lignin conversion products were filtered, it was observed that the majority of the catalyst remained in the lignin conversion reactor (500). Finer particles of catalyst were observed on the filter paper. It was also surprisingly observed that, where higher rates of lignin conversion were attained, less catalyst was removed from the lignin conversion reactor as evidenced by less catalyst present on the filter paper.

It is believed that the settling velocity of the catalyst particles is greater than the velocity of the removal of lignin conversion products from the lignin conversion reactor (500) through the dip tube (610). This results in the surprising and advantageous retention of catalyst in the lignin conversion reactor. It is further believed that the fibrous, Velcro®-like nature of the lignin-rich composition in the slurry comprised of lignin will attach itself to the catalyst particles (625) and remove them from the lignin conversion reactor where lower levels of lignin conversion are achieved. It is further believed that, where removal of all or a portion of the catalyst from the lignin conversion reactor is desired, all or a portion of the catalyst can be removed from the Parr reactor by decreasing the diameter and length of the dip tube, thereby increasing the velocity of the removal of lignin conversion products from the Parr reactor to a level greater than that of the settling velocity of the catalyst.

Bubble Column Reactor

Although the process can be operated where the lignin conversion reactor is a continuous stir tank reactor (CSTR), the CSTR requires a high amount of energy input, and the high pressure required to convert lignin on a continuous basis results in an unreasonably large reactor when utilizing a CSTR. It has been discovered that a bubble column reactor requires less energy input and allows for a smaller reactor for a continuous lignin conversion process.

One alternative to the CSTR is the ebullating bed reactor, as described in U.S. Pat. No. 4,240,644. One version of ebullated bed is a bubble column reactor. A bubble column reactor consists of at least one vertical cylinder at least partially filled with liquid. Gas is fed to the bottom of the cylinder through a gas feed tube causing a turbulent upward stream of bubbles. In a preferred embodiment the gas may be hydrogen or nitrogen. In a preferred embodiment the liquid may comprise water. In a further embodiment the liquid may comprise a hydrogen donor. The gas flow could be nitrogen or hydrogen gas, at a sufficient rate to keep the catalyst particles fluidized within the liquid components of the reactor.

In a preferred embodiment, the bubble column reactor will also comprise a gas distributor at the bottom of the vertical cylinder to allow for even distribution of gas bubbles. A preferred gas distributer is comprised of a material which is not corroded by the reactants, such as a stainless steel mesh.

A slurry comprised of lignin can be fed to the bottom of the vertical cylinder through a slurry feed tube. The amount of slurry comprised of lignin fed to the bubble column reactor can be varied to achieve increased rates of lignin conversion as described in the experimental section below based on temperature, pressure, hydrogen flow, amount of catalyst and residence time.

In one embodiment a plurality of catalysts may be charged to the bubble column reactor through the slurry feed tube. In another embodiment a plurality of catalysts may be charged directly to the bubble column reactor prior to charging the hydrogen and/or slurry comprised of lignin to the bubble column reactor.

The reactor scheme for the bubble column may also include a second column for the disengagment of the solid unreacted lignin and catalyst to flow by gravity into the bottom of the bubble column or ebullating reactor and be recontacted with fresh gas.

The bubble column reactor may also comprise a heating element which allows for regulation of the bubble column reactor temperature. Preferably this heating element comprises a plurality of heating coils wrapped around the vertical cylinder. In a preferred embodiment the bubble column reactor temperature is between 220° C. and 350° C. The reactor conditions of pressure and temperature should be selected so as to prevent char formation as discussed earlier.

Bubble column reactor pressure may be varied based upon the bubble column reactor temperature and gas flow rate as described in the experimental section below. In a preferred embodiment the bubble column reactor pressure is between 150 bar and 230 bar.

A dip tube may be inserted at the top of the vertical cylinder for removing a plurality of the lignin conversion products to a products receiver.

In one embodiment the bubble column reactor may consist of a plurality of vertical cylinders, each having a separate gas feed tube, a separate slurry feed tube and a separate dip tube.

What was found is that, by utilizing a bubble column reactor instead of a CSTR, significant amounts of energy savings can be attained due to the lack of a separate stirring element. Additionally, the bubble column results in higher rates of conversion than a CSTR while converting the slurry comprised of lignin to similar products.

BUBBLE COLUMN REACTOR EXPERIMENTS

The following procedures were applied to all the experiments, unless differently specified. De-ionized water was added to a lignin-rich composition obtained from the pretreatment of ligno-cellulosic biomass to obtain a slurry comprised of lignin having a dry matter solids content of 5 weight percent of the mass of the slurry comprised of lignin. The mixture was inserted into a blender (Waring Blender, model HGBSS6) and thoroughly mixed intermittently at thirty second intervals (thirty seconds of mixing followed by thirty seconds without mixing) for 10 min. to reach a visually homogenous slurry. (See Experimental establishing the ability of the Waring HGBSS6 Blender to homogenously disperse on a quantitative basis). The homogeneity of the slurry comprised of lignin was evaluated by eye.

The slurry comprised of lignin was inserted into a mix tank with constant agitation. The mix tank was a stainless steel, dish bottom tank with a bottom discharge port connected to a Chandler Quizix QX dual syringe pump having two pump cavities. Inlet ball valves were inserted between the mix tank and the two pump cavities of the Chandler Quizix QX dual syringe pump. The Chandler Quizix QX dual syringe pump was connected by stream (1510) to a bubble column reactor having an inside diameter (1540) of one inch, a height (1545) of thirty inches, a heating element (1550), a gas distributor (1570) comprised of stainless steel mesh having a length of two inches, a slurry feed tube (1560) at the bottom of the column having a length of six inches for feeding the lignin slurry to the bubble column reactor, and a dip tube (1565) having a length of eight inches connected to a transfer line (1580) at the top of the bubble column reactor for removal of reaction products to a products receiver. The products receiver was maintained at the same pressure as the bubble column reactor. The bubble column reactor further contained a vent (1520) connected to a rupture disk (1521) and a pressure transducer (1522). The bubble column reactor further contained a thermal well (1590) for measuring temperature inside the bubble column reactor during the experiment.

The slurry comprised of lignin was passed from the mix tank through the Chandler Quizix QX dual syringe pump and into the bubble column reactor by opening and closing the inlet and outlet valves in a manner that allowed the lignin slurry to pass continuously into the bubble column reactor.

The inventors conducted a set of seven experiments. The results of these experiments are summarized below in Table 3 and Table 4.

Bubble Column Experiment 1

For Experiment 1, 43 g of Raney Nickel catalyst (1500) was charged directly to the bubble column reactor, along with 150 g of liquid water, prior to beginning the experiment. Hydrogen was swept through the system continuously at a gas flow rate of 300 scc/m through the gas feed tube (1530) and into the gas distributor (1570). The bubble column reactor was heated to a bubble column reactor temperature of 310° C.

to achieve a target bubble column reactor pressure of 165.5 bar. Slurry comprised of lignin was fed to the bubble column reactor at a rate of 3 mL/min. The slurry comprised of lignin was continuously fed to and removed from the bubble column reactor for a period of five hours or a total of 4.1 residence cycles of slurry comprised of lignin through the reactor. The total amount of slurry comprised of lignin passed through the system was 45 g. When the inventors concluded the experiment, 11.1293 g of un-reacted slurry comprised of lignin remained in the bubble column reactor, however, in removing the un-reacted slurry comprised of lignin from the bubble column an unknown quantity was spilled.

Figure 9:
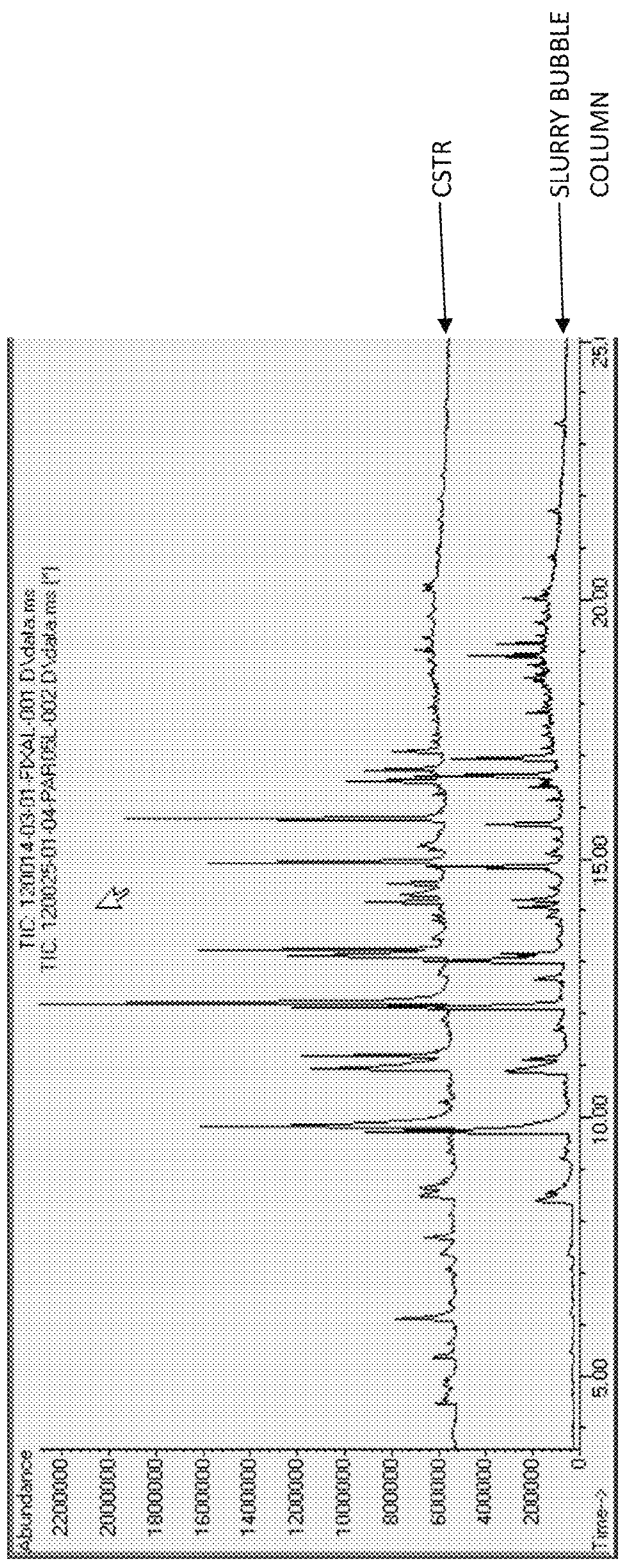
FIG. 9 shows the ability of a bubble column to convert the slurry comprised of lignin to lignin conversion products comparable to those attained from a continuous stir tank reactor.

What was observed was that the lignin conversion products were phenol oils that were nearly identical in composition as measured by G.C. Mass Spectrometer to the phenol oils produced during a lignin conversion process in a continuous stir tank reactor (CSTR) (See FIG. 9). Conversion rate of the slurry comprised of lignin was 75.27%, not taking into account the unknown quantity of un-reacted slurry comprised of lignin which was spilled.

Bubble Column Experiment 2

For Experiment 2, the inventors increased the bubble column reactor temperature from 310° C. to 318° C. The constant amount of slurry comprised of lignin present in the bubble column reactor after reaching assumed steady state during the experiment was 15.2587 g. All other conditions remained the same as in Experiment 1. When the inventors concluded the experiment, 15.2587 g of un-reacted slurry comprised of lignin remained in the bubble column reactor.

What was observed was that the increased bubble column reactor temperature resulted in a rate of conversion of the slurry comprised of lignin of 66.09%.

Bubble Column Experiment 3

For Experiment 3, the inventors reduced the amount of catalyst charged to the bubble column reactor from 43 g to 21.5 g. The constant amount of slurry comprised of lignin present in the bubble column reactor after reaching assumed steady state during the experiment was 16.5924 g. All other conditions remained the same as in Experiment 2. When the inventors concluded the experiment, 16.5924 g of un-reacted slurry comprised of lignin remained in the bubble column reactor.

What was observed was that the reduced catalyst in the bubble column reactor resulted in a reduced rate of conversion of the slurry comprised of lignin of 63.13%.

Bubble Column Experiment 4

For Experiment 4, the inventors increased the bubble column reactor pressure from 166.49 bar to 172.4 bar and reduced the rate of slurry flow from 3 mL/min to 2 mL/min. Total run time was increased to six hours and forty minutes, and total input of the slurry comprised of lignin was decreased to 40 g. The number of turns of slurry comprised of lignin through the bubble column reactor decreased to 3.62. The total amount of slurry comprised of lignin present in the bubble column reactor after reaching assumed steady state during the experiment was 18.4116 g. All other conditions remained the same as in Experiment 2. When the inventors concluded the experiment, 18.4116 g of un-reacted slurry comprised of lignin remained in the bubble column reactor.

What was observed was that the reduced slurry flow resulted in a lower rate of conversion of the slurry comprised of lignin of 53.97%.

Bubble Column Experiment 5

For Experiment 5, the inventors further reduced the rate of slurry flow from 2 mL/min to 1.2 mL/min. Total run time was increased to ten hours, and total input of the slurry comprised of lignin was decreased to 36 g. The number of residence cycles of slurry comprised of lignin through the reactor decreased to 3.26. The total amount of slurry comprised of lignin present in the bubble column reactor after reaching assumed steady state during the experiment was 14.2125 g. All other conditions remained the same as in Experiment 4. When the inventors concluded the experiment, 14.2125 g of un-reacted slurry comprised of lignin remained in the bubble column reactor.

At times of four hours, eight hours, and ten hours, the products receiver was de-pressurized and discharged. After four hours, the products receiver contained 0.89 g of phenol oils. After eight hours the products receiver contained 3.25 g of phenol oils. After ten hours the products receiver contained 0.97 g of phenol oils. Upon completion of the experiment, it was further observed that 2.4 g of phenol oils remained present in the transfer line. When the residual solids were drained from the bubble column reactor, filtered, washed with acetone and Rotovapped, it was further observed that 1 g of phenol oils was present in the residual solids. Total, 8.51 g of phenol oils were collected resulting in a phenol oils yield % based on the amount of converted slurry comprised of lignin of 39.06%. The phenol oils yield % based on the amount of slurry comprised of lignin charged to the bubble column reactor was 23.64%.

What was observed was that, despite the reduced slurry flow, the increased total run time resulted in a higher rate of conversion of the slurry comprised of lignin of 60.52%

Bubble Column Experiment 6

For Experiment 6, the inventors increased the gas flow through the reactor from 300 scc/m to 600 scc/m resulting in a bubble column reactor pressure increase from 172.4 bar to 187.2 bar. Total run time was also increased to twelve hours. This resulted in an increased total input of slurry comprised of lignin of 72 g. The number of residence cycles of slurry comprised of lignin through the reactor increased to 7. The total amount of slurry comprised of lignin present in the bubble column reactor at any one time during the experiment was 23.5214 g. All other conditions remained the same as in Experiment 4. When the inventors concluded the experiment, 23.5214 g of slurry comprised of lignin remained in the bubble column reactor.

At times of two hours forty minutes, five hours twenty minutes, eight hours, ten hours forty minutes and twelve hours the products receiver was de-pressurized and discharged. After two hours forty minutes the products receiver contained 1.43 g of phenol oils. After five hours twenty minutes the products receiver contained 3.27 g of phenol oils. After eight hours the products receiver contained 2.64 g of phenol oils. After ten hours forty minutes the products receiver contained 4.7 g of phenol oils. After twelve hours the products receiver contained 3.57 g of phenol oils. Upon completion of the experiment, it was further observed that 9.29 g of phenol oils remained present in the transfer line. When the residual solids were drained from the bubble column reactor, filtered, washed with acetone and Rotovapped, it was further observed that 1.05 g of phenol oils was present in the residual solids. Total, 25.95 g of phenol oils were collected resulting in a phenol oils yield percentage based on the amount of converted slurry comprised of lignin of 53.53%. The phenol oils yield % based on the amount of slurry comprised of lignin charged to the bubble column reactor was 36.04%.

What was observed was that the increased gas flow rate resulted in a higher rate of conversion of the slurry comprised of lignin of 67.33%. It was further observed that increasing the gas flow rate increased the phenol oils yield percentage both based upon the amount of converted slurry comprised of lignin and on the amount of slurry comprised of lignin charged to the bubble column reactor.

Bubble Column Experiment 7

For Experiment 7, the inventors increased the bubble column reactor temperature to 335° C. resulting in an increased bubble column reactor pressure of 207.9 bar. The inventors also increased the amount of catalyst charged to the bubble column reactor to 85 g and the rate of slurry flow from 2 mL/min to 3 mL/min. Total run time was decreased to five hours. This resulted in a decreased total input of slurry comprised of lignin of 45 g. The number of residence cycles of slurry comprised of lignin through the reactor decreased to 4.3. The total amount of slurry comprised of lignin present in the bubble column reactor at any one time during the experiment was 12.082 g. All other conditions remained the same as in Experiment 6. When the inventors concluded the experiment, 12.082 g of slurry comprised of lignin remained in the bubble column reactor.

At times of two hours, four hours, and five hours, the products receiver was de-pressurized and discharged. After two hours the products receiver contained 2.69 g of phenol oils. After four hours the products receiver contained 1.34 g of phenol oils. After five hours the products receiver contained 0.36 g of phenol oils. Upon completion of the experiment, it was further observed that 11.92 g of phenol oils remained present in the transfer line. When the residual solids were drained from the bubble column reactor, filtered, washed with acetone and Rotovapped, it was further observed that 1.25 g of phenol oils was present in the residual solids. Total, 17.56 g of phenol oils were collected resulting in a phenol oils yield % based on the amount of converted lignin of 53.34%. The phenol oils yield % based on the amount of slurry comprised of lignin charged to the bubble column reactor was 39.02%.

What was observed was that increasing the bubble column reactor temperature, amount of catalyst and gas flow resulted in a higher rate of conversion than any of the previous six experiments. Further, it was observed that the higher rate of conversion resulted in an increased phenol oils yield % based on the amount of slurry comprised of lignin charged to the bubble column reactor, despite not resulting in an increased phenol oils yield % based on the amount of converted lignin.

TABLE 3

| Exp. No. | Temp. (° C.) | Pressure (bar) | H2O (R) | Catalyst (g) | Slurry Flow (mL/min) | Slurry (wt %) | H2 Flow (scc/m) | Total Lignin in B.C. | Residence Cycles |
|---|---|---|---|---|---|---|---|---|---|
| BC1 | 310 | 165.5 | 150 | 43 | 3 | 5 | 300 | * | 4.1 |
| BC2 | 318 | 165.5 | 150 | 43 | 3 | 5 | 300 | 15.2587 | 4.1 |
| BC3 | 318 | 165.5 | 150 | 21.5 | 3 | 5 | 300 | 16.5924 | 4.1 |
| BC4 | 318 | 172.4 | 150 | 43 | 2 | 5 | 300 | 18.4116 | 3.62 |
| BC5 | 318 | 172.4 | 150 | 43 | 1.2 | 5 | 300 | 14.2125 | 3.26 |
| BC6 | 318 | 187.2 | 150 | 43 | 2 | 5 | 600 | 23.5214 | 7 |
| BC7 | 335 | 207.9 | 150 | 85 | 3 | 5 | 600 | 12.082 | 4.3 |

* Total slurry comprised of lignin in the bubble column reactor is equivalent to the amount of unconverted lignin slurry remaining in the bubble column reactor upon shutdown. In BC1, 11.1293 g of unconverted lignin remained in the bubble column reactor, however an unknown quantity of un-reacted lignin was spilled upon removal from the bubble column reactor at the end of the Experiment resulting in inaccurate measurements.

TABLE 4

| Exp. No. | Rate of Conversion (%) | Total Phenol Oils (g) | Phenol Oils Yield % (converted) | Phenol Oils Yield % (charged) | Catalyst Remaining in Reactor (g) | Lignin Remaining in Reactor (g) | Catalyst/Lignin Remaining in Reactor (g) |
|---|---|---|---|---|---|---|---|
| BC1 | * | N/A | N/A | N/A | 24.03 | * | 2.16/1 |
| BC2 | 66.09 | N/A | N/A | N/A | 19.71 | 15.2587 | 1.29/1 |
| BC3 | 63.13 | N/A | N/A | N/A | 15.83 | 16.5924 | 0.95/1 |
| BC4 | 53.97 | N/A | N/A | N/A | 29.71 | 18.4116 | 2.16/1 |
| BC5 | 60.52 | 8.51 | 39.06 | 23.64 | 27.62 | 14.2125 | 1.94/1 |
| BC6 | 67.33 | 25.95 | 53.53 | 36.04 | 30.81 | 23.5214 | 1.31/1 |
| BC7 | 73.15 | 17.56 | 53.34 | 39.02 | 56.79 | 12.082 | 4.7/1 |

* 11.1293 g of unconverted lignin remained in the reactor resulting in a rate of conversion in Experiment BC1 of 75.27%, however an unknown quantity of un-reacted lignin was spilled upon removal from the bubble column reactor at the end of the Experiment resulting in inaccurate measurements.

The lignin conversion process is considered a continuous process because the lignin conversion products are removed from the lignin conversion reactor (500) in a continuous manner. The reactants, such as the component of the slurry comprised of lignin are generally introduced into the lignin conversion reactor in a continuous manner as well. "A continuous manner" does not mean that that feedstock or products are continuously introduced or removed at the same rate. For example, when only one piston pump is used, the slurry comprised of lignin is introduced into the lignin conversion reactor (500) in steady aliquots or pulses. Thus there are moments, when there is no product entering the lignin conversion reactor. But over time, the mass introduced into the lignin conversion reactor equals the mass removed from the lignin conversion reactor. One distinguishing feature between a continuous and a batch process is that, in the continuous process, the reaction is occurring or progressing at the same time that either the reactant feeds are introduced into the lignin conversion reactor and/or the lignin conversion products are removed from the lignin conversion reactor. Another way to state this that the conversion (e.g. deoxygenating, or hydrogenating) in the lignin conversion reactor occurs while simultaneously, or at the same time, removing at least a portion of the lignin conversion products from the lignin conversion reactor. Such removal is done in a continuous manner which includes a pulse removal.

The invented process converts the lignin in the feedstock to several different product types. As described later, the process conditions can be set to produce one class of compounds at the expense of another class of compounds.

The lignin conversion can be considered as a deoxygenation of lignin. The lignin will not convert to a single product, but to a plurality of lignin conversion products. The feedstock comprising lignin is exposed to additional hydrogen ($H_2$) gas which can be added in the conventional manner according to the temperature and pressure of the lignin conversion reactor. The plurality of lignin conversion products may be void of ethylene glycol or propylene glycol.

There will also be a first catalyst present in the lignin conversion reactor (500). The reason it is called a first catalyst is that there may be a second catalyst added to the lignin conversion reactor or a second catalyst may be used to further react the lignin conversion products in a different step. While there may be a second catalyst, it is possible in one embodiment that there is only one catalyst, the first catalyst. The lignin conversion reactor may be void a second catalyst.

The lignin conversion products may comprise compounds which are found in jet fuel, or the lignin conversion products may be further converted to compounds comprising jet fuel.

The first catalyst can be any one of the catalysts known to catalyze the reaction of hydrogen with lignin. The first catalyst used in the conversion process is preferably a sponge elemental metal catalyst comprising at least one sponge elemental metal created by the Raney process as described and claimed in U.S. Pat. No. 1,628,190, the teachings of which are incorporated in their entirety.

The process as claimed creates an alloy of at least a first metal and a second metal dissolves the second metal out of the first metal, leaving behind a finely divided elemental first metal with high surface area. This high surface area is often described as a sponge structure. The preferred first catalyst of the lignin conversion process is known as Raney Nickel, or where the finely divided elemental metal is nickel. Another preferred metal is a metal selected from the group consisting of palladium, platinum, nickel, ruthenium, rhodium, molybdenum, cobalt, and iron. Because water is a feature of the reaction, the catalyst structure, particularly its support must be hydrothermally stable. Due to the heterogeneous nature, at least a portion of the first catalyst is present as a plurality of particles, or in particle form. At a least a portion of the first catalyst, if not all of the first catalyst, is not present as a fixed bed.

The first catalyst may or may not be supported or unsupported, but is generally not present as a fixed bed. If a fixed bed catalyst is used, the feedstock should be present as a liquid as opposed to a slurry so that solids do not plug the pores of the fixed bed. The contemplation of a fixed bed is part of the conception because it is believed that many of the enabling principles of this process are applicable to both a slurry feedstock and a liquid feedstock without solids, or at least less than 1% solids by weight, of a slurry where the solids are present in a size less than the pores of the fixed bed.

The amount of the first catalyst can be expressed by the weight of the elemental nickel to the dry weight of the lignin feedstock, where the weight of the elemental nickel to the dry weight of the lignin in the feedstock should be in the range of about 0.25 to about 2.0, with the range of about 0.3 to about 1.5 being more preferred with at least about 0.5 to 1.0 being the most preferred. In one embodiment, the process is void of a catalytic amount of a second catalyst.

The second catalyst, if used, can be any of the standard hydrogenation catalysts known, with the preferred second catalyst being the same as the first catalyst. When the second catalyst is the same as the first catalyst, the amount of the second catalyst is the same as the amount of the first catalyst. When deoxygenation and dehydrogenation are conducted simultaneously in the same vessel, there is no additional second catalyst added as the first catalyst and its amount becomes the second catalyst for the purposes of the dehydrogenation reaction.

There is also a preferred introduction of a third catalyst, which is different from the first and second catalysts. The preferred third catalyst is a Zeolite creating heterogeneous cites for the reactions to progress in an acidic environment.

The plurality of conversion products preferably comprise at least one product selected from the group consisting of carbon dioxide, methane, ethane, phenols, benzene, toluene, and xylenes.

It should be evident from FIG. 4 how the reaction process can be operated as a CSTR—continuous stirred tank reactor.

The invention taught by the in situ separation using a dip tube is applicable to almost any solid—liquid where the solids are present as finely dispersed particles. This aspect of the invention is not limited to a lignin conversion process.

Another embodiment of the process is that the plurality of lignin conversion products are cooled after leaving the reactor separating the vapor from the liquid and solids, with the back pressure regulator (700) located after the liquid solids separator (600), the pressure of the lignin conversion process can now be controlled.

The temperature of the lignin conversion products generated by the lignin conversion process are substantially greater than the temperature of the steam, soaking and fermentation processes of the pre-treatment and carbohydrate conversion processes that would precede the lignin conversion process. The inventors clearly contemplate that in the integrated or co-sited operation that the heat from the lignin conversion products would be transferred to soaking, steam pretreatment, hydroylsis, and/or fermentation processes of the pre-treatment process.

Once these liquid lignin conversion products are obtained, they can then be subsequently converted to a number of different chemical feedstocks and intermediates. One preferred intermediate is at least one polyester intermediate selected from the group consisting of ethylene glycol, terephthalic acid, and isophthalic acid. Once the intermediate is made, the conversion of the intermediate to polyester and subsequent articles such as soft drink bottles, beer bottles, and other packaging articles can be accomplished using the conventional techniques known today and those yet to be invented.

Since the lignin often comes with intractable carbohydrates, it may be preferable to treat the feedstock first with a carbohydrate conversion step to obtain carbohydrate conversion products. In a preferred embodiment, the carbohydrate conversion products are selected from the group consisting of alcohols, polyols, glucans, gluco-lignins and cellulose.

Fermentation is one such carbohydrate conversion step. Another carbohydrate conversion step and embodied in FIG.

1 is to create a slurry feedstock comprised of carbohydrates and lignin, feed it to a carbohydrate conversion reactor as described in US2011/312487 and US2011/312488 and US2011/0313212 by pressuring the slurry feedstock as described in this specification and feeding it into a first reaction zone and a) contacting, the lignin slurry feedstock in a continuous manner, in a first reaction zone, with hydrogen, water, and a catalyst to generate an effluent stream comprising at least one polyol, hydrogen, water and at least one co-product, wherein the hydrogen, water, and feedstock comprising cellulose are flowing in a continuous manner, and wherein the catalyst in the first reaction zone consists essentially of at least two active metal components selected from the group consisting of:

(i) Mo, W, V, Ni, Co, Fe, Ta, Nb, Ti, o, Zr and combinations thereof wherein the metal is in the elemental state or the metal is a carbide compound, a nitride compound, or a phosphide compound;

(ii) Pt, Pd, Ru, and combinations thereof wherein the metal is in the elemental state; and (iii) any combination of (i) and (ii);

b) separating hydrogen from the effluent stream and recycling at least a portion of the separated hydrogen to the reaction zone;

c) separating water from the effluent stream and recycling at least a portion of the separated water to the reaction zone; and d) recovering the polyols from the effluent stream.

After recovering the converted carbohydrates, such as the polyols from the effluent stream, to create a secondary feedstock stream comprising lignin, the secondary feedstock stream comprising lignin can be again optionally pressurized and fed into the lignin conversion reactor (500) to convert lignin into the phenols and other component in the plurality of lignin conversion products.

In a preferred embodiment, the polyols, such as ethylene glycol and propylene glycol may be used as a hydrogen donor to convert the lignin to lignin conversion products. In another embodiment, the hydrogen from the effluent stream may be used as a source of hydrogen to convert the lignin to lignin conversion products. Also, the water from the effluent stream may be recycled or reused as treatment water for pretreating the ligno-cellulosic biomass feedstock.

Now that the fundamental operations have been explained, one can turn to FIG. 1 to describe one embodiment and its variations. As depicted in FIG. 1, the conversion of the ligno-cellulosic biomass can begin with either pre-treated ligno-cellulosic biomass (20A or 20B) or untreated ligno-cellulosic biomass (10A or 10B). The A stream is fed into an optional carbohydrate conversion process to convert the carbohydrates to useful products prior to converting the lignin. The chosen feedstock enters the carbohydrate conversion reactor (100) via stream (110). Additional reactants, such as hydrogen are added into (120). If the ligno-cellulosic biomass is added as a slurry and a catalyst is used, the handling principles described creating the continuous process apply and reduce this process to practice as well. After conversion, the carbohydrate conversion products are passed from the carbohydrate conversion reactor (100) to carbohydrate conversion product recovery (200) via stream (210). There can be two types of carbohydrate conversion products, one being gas exiting via (220). This gas could be methane which can be converted to hydrogen by known technologies such as steam reforming. The hydrogen would be used either to convert more carbohydrates or lignin by introducing the hydrogen into lignin conversion reactor (500) via stream (520). Should the embodiment produce ethylene glycol, that ethylene glycol would be transferred via stream (230) to a polyester manufacturing facility which would convert the ethylene glycol into polyester resin which is later converted to finished polyester articles such as preforms and polyester bottles.

The lignin from the carbohydrate conversion process enters the lignin slurry creation step (300) via stream (310). The embodiment without the first carbohydrate conversion step is depicted by streams (20B) and (10B) respectively. As contemplated by the inventors, these could directly feed, and have been proven to be continuously converted when fed directly into the slurry creation step (300). Makeup water or other solvent is added via stream (320) with the optional vacuum being applied through stream (330).

If the ligno-cellulosic feedstocks of either (20B) or (10B) are already in a slurry form, step (300) can be skipped and the streams (10B) or (20B) fed directly into the slurry pump or slurry pumps (400) via stream (410). The pumping system as described above increases the pressure of the slurry to greater than the reactor conversion pressure of the lignin conversion reactor (500). After pressurizing the slurry to greater than the reactor conversion pressure of the lignin conversion reactor, the slurry pump will discharge the slurry comprised of lignin through an outlet valve (450) to the lignin conversion reactor (500) through stream (510). Lignin conversion reactor (500) will contain the lignin slurry and at least the first catalyst. Hydrogen will enter the lignin conversion reactor (500) at pressure through stream (520). As a CSTR, the lignin conversion products are passed up through dip tube (610), with the catalyst settling back down into the lignin conversion reactor (500). Vessel (600) is the liquid solids separator, with the gas by-products exiting the separation vessel (600) via stream (710) and passing into the back pressure regulator (700) which controls the pressure of the whole system. After reducing the pressure, the gasses are passed through stream (720). If carbohydrates were introduced into the lignin conversion reactor, then stream (720) will contain methane, a conversion product of the carbohydrates, thus the carbohydrate conversion process has been done in situ with the lignin conversion. The methane can be further converted to hydrogen through steam reforming for example and re-used in the process, thus making the process at least partially self-sufficient in hydrogen.

The solids from the lignin conversion process are separated from the liquids in step (600) with the solid passing in stream (620) and the liquids passing to the BTX conversion step (800) via stream (810). Stream (650) of FIG. 3 shows the separation of water from the lignin conversion process. While the water will be present in the liquid phase, there may be some water vapor present in (720) as well. As depicted in FIG. 1, in this embodiment, at least a portion of the water is re-used to create or supplement the slurry comprised of lignin. As the lignin conversion process is a net water producer, some water will be purged in stream (620).

The conversion of phenols to BTX is a well known chemistry with several routes being available. As the lignin conversion process produces predominantly phenols, the conversion of phenols by the known routes is considered well within the scope of one of ordinary skill. Once the BTX (benzene, toluene, xylenes) is formed it can be passed to a conversion step to convert the BTX to terephthalic acid, react the terephthalic acid with ethylene glycol and make polyester resin and subsequently articles from polyester resin (900) via stream (910). It is again well within the scope of one of ordinary skill to convert these products to terephthalic acid, react the terephthalic acid with ethylene glycol to make polyester resin and subsequently articles from the polyester resin such as films, trays, preforms, bottles and jars.

Integrated Process Experiments

Material Preparation

The experiments used a composition obtained from wheat straw as a starting raw material.

The raw material was subjected to a soaking treatment in water at a temperature of 155° C. for 65 minutes then steam exploded at a temperature of 190° C. for 4 minutes.

The steam exploded material and the liquids from soaking material were mixed together and subjected to enzymatic hydrolysis, fermentation to ethanol and distillation.

Detailed parameters used are considered not relevant for the experiments, provided that the percentage content of the composition is preserved.

The mixture of liquid and solids after distillation was pressed at 15 bar and at a temperature of 80° C. to obtain a dense and compact solid, having a dry matter content of 55% and characterized by the following composition on a dry matter basis.

TABLE 5

LIGNIN FEEDSTOCK ANALYSIS

| ELEMENT | Percentage content |
| --- | --- |
| Ash | 13.04 |
| Lignin | 49.71 |
| Glucan | 21.77 |
| Xylan | 6.81 |
| Other compounds | 8.67 |

The lignin-rich composition was subjected to a temperature lower than 0° C. and kept frozen until experiments execution.

Lignin Conversion Procedure

The following procedures were applied to all the experiments not using the bubble column, unless differently specified.

Frozen lignin-rich composition was naturally unfrozen until reaching a temperature of 20° C.

De-ionized water was added to the lignin-rich composition to reach the final lignin-rich composition concentration in the slurry planned in each experiment. The mixture was inserted into a blender (Waring Blender, model HGBSS6) and thoroughly mixed intermittently (e.g. pulsed on for 30 sec, left off for 30 sec) for 10 min to reach a homogeneous slurry. The homogeneity of the slurry was evaluated by eye.

The slurry was inserted into a mix tank with constant agitation. The mix tank was a stainless steel, dish bottom tank with a bottom discharge port connected to a Chandler Quizix QX dual syringe pump equipped with full port ball valves, connected to the lignin conversion reactor. The pump discharge was connected to the reactor with tubing.

The lignin conversion reactor was a Parr 4575 reactor equipped with a dual 45° pitched turbine blade, cooling coil, separate gas and slurry feed ports and a discharge dip tube. The reactor was charged with water (~220 mL) and catalyst (Johnson Matthey A-5000 sponge catalyst) according to the experimental conditions of each experiment and sealed. The weight of catalyst introduced is indicated as the ratio between the weight of the catalyst and the weight of dry matter of the lignin-rich composition added to the lignin conversion reactor in one residence time. Hydrogen at a temperature of 20° C. was inserted into the lignin conversion reactor to reach a pressure of 48.3 bar. The lignin conversion reactor was heated to a temperature corresponding to 90% of the reaction temperature and continuous flow of Hydrogen was started into the lignin conversion reactor. The lignin conversion reactor was connected to a products receiver, maintained at 25° C. The pressure was measured by means of a pressure transducer (Ashcroft Type 62) connected to the lignin conversion reactor and controlled by means of a back-pressure regulator (Dresser Mity Mite 5000, model 91) placed downstream of the products receiver. Temperature was increased to the reaction temperature and the flow of slurry comprised of lignin was introduced into the lignin conversion reactor. The slurry flow rate was calculated for obtaining the residence time of the lignin feed in the reactor in each experiment at the operating conditions. After a time corresponding to 3 residence times steady conditions were considered to be reached and solid and liquid reaction products were collected into the receiver for a time corresponding to 1 residence time. The receiver was depressurized to atmospheric pressure, the non-gaseous reaction products were extracted with methyl tert-butyl ether organic solvent, filtered, and the liquid phases were separated by a separatory funnel.

This system was continuously operated many times without shutting down for up to 2 shifts (approximately 16 hours).

Experiments were conducted according to the described procedure. Experimental parameters are reported in Table 6.

TABLE 6

EXPERIMENTAL PARAMETERS

| | | H2 | | Flow Rate | | Lignin-rich composition | Residence | Catalyst to Lignin-rich | Unreacted Lignin | % |
| --- | --- | --- | --- | --- | --- | --- | --- | --- | --- | --- |
| Exp. No. | Temp (° C.) | Flow (sccm) | Press. (bar) | Slurry (mL/min) | Solids (g/min) | Concentration (wt %) | time (min) | composition ratio | (% of Theoretical) | Catalyst Loss |
| 1 | 340 | 150 | 156.1 | 2.8 | 0.42 | 15 | 53 | 0.50 | | |
| 2 | 340 | 500 | 173.4 | 5.6 | 0.84 | 15 | 26 | 2.60 | | |
| 3 | 340 | 500 | 173.4 | 2.8 | 0.42 | 15 | 51 | 1.25 | | |
| 4 | 305 | 100 | 122.4 | 3.8 | 0.19 | 5 | 45 | 0.25 | 3.1 | 13.3 |
| 5 | 325 | 100 | 166.5 | 3.8 | 0.19 | 5 | 42 | 0.25 | 0.2 | 1.7 |
| 6 | 305 | 800 | 122.4 | 3.8 | 0.19 | 5 | 45 | 2.00 | 0.6 | 1.3 |
| 7 | 325 | 100 | 166.5 | 2.3 | 0.12 | 5 | 70 | 0.25 | 0.3 | 1.1 |
| 8 | 305 | 100 | 122.4 | 3.8 | 0.57 | 15 | 45 | 2.00 | 20.8 | 18.4 |

The experiments produced the following main products:

TABLE 7

Lignin Conversion Products for Table 6, Experiment 4

| Product ID | Relative Amount (Area % of G.C.) | | | | |
|---|---|---|---|---|---|
| | Exp 4 | Exp 5 | Exp 6 | Exp 7 | Exp 8 |
| 2-Methoxyphenol | 10.908 | 13.87 | 6.337 | 11.641 | 6.578 |
| 2,6 Dimethoxyphenol | 8.673 | 9.69 | 5.918 | 7.229 | 5.315 |
| 4-Ethyl-2-methoxy-phenol | 8.139 | 9.728 | 8.729 | 9.994 | 8.802 |
| 2,6-Dimethoxy-4-propylphenol | 5.764 | 3.063 | 8.458 | 5.261 | 7.637 |
| 2-Methoxy-4-propyl-phenol | 5.118 | 2.322 | 5.417 | 4.042 | 5.798 |
| 4-Ethylphenol | 4.563 | 5.335 | 5.265 | 6.228 | 5.081/1.38 |
| 1-(4-Hydroxy-3,5-dimethoxyphenyl)-ethanone | 4.288 | 2.943 | | 1.868 | 1.635 |
| 2,6-Dimethoxy-4-ethylphenol | 3.859 | 3.529 | 6.363 | 2.634 | 3.02 |
| Cyclopentanone | 2.57 | 1.667 | 1.764 | 1.087 | |
| 2-Methyl-2-Cyclopenten-1-one | 2.233 | 2.525 | | 2.431 | 1.244 3 methyl? |
| 2-Methoxy-4-methylphenol | 2.153 | 2.576 | 2.12 | 2.18 | 1.377 |
| 2-methyl-Cyclopentanone | 2.142 | | 1.772 | 2.194 | 1.208 |
| Phenol | 1.932 | 2.808 | | 2.753/2.054 | |
| 2,6-Dimethoxy-methylphenol | 1.858 | 2.504 | 2.107 | 1.975 | 1.365 |
| 2,6-Dimethoxy-4-(2-propenyl)-phenol | 1.239 | 1.184 | 2.987 | 1.192 | 1.179 |
| 2-Methyl-Cyclopentanone | | 1.324 | | | 1.208 |
| >C20 Aliphatic | | | 2.114 | | |
| >C20 Aliphatic | | | 1.902 | | |
| Formic Acid, 1,1, dimethlyehtyl ester | | | 1.406 | | |
| Cyclohexanol | | | 1.263 | | |
| >C10 Aliphatic | | | 1.146 | | |
| >C20 Aliphatic | | | 1.131 | | |
| 2,3-Dimethyl-2-Cyclopenten-1-one | | | | 1.329 | |
| Eugenol | | | | 1.086 | 1.435 |
| Cyclohexanone, 3-ethenyl | | | | 1.074 | 1.559 |
| Flopropione | | | | | 1.471 |
| >C20 Aliphatic | | | | | 1.228 |

[1]Those unidentified general compounds had a 20% match in the library with the listed compound so they are noted only by the number of carbons.

Recycle of Waste Water Treatment

What has also been discovered is that the lignin conversion process of catalytic hydrogenation removes much of the contaminants from the water of the stillage entering the process.

This was easily demonstrated by analyzing the chemical oxygen demand, also known as CODs of the stillage from the fermentation (carbohydrate conversion process) prior to the lignin conversion process and then analyzing the CODs from the water phase after the lignin conversion process.

Observationally, the untreated stillage in a glass sample container appeared as a dark brown homogeneous solution. Prior to being processed in the lignin conversion process the liquid fraction was dark brown to black, indicating a large amount of soluble contaminants. After passing the water through the lignin conversion process (as part of the ligno-cellulosic biomass feedstock) the water was separated from the organic products. The water was no longer dark, but an amber straw gold.

When measured for CODs, the untreated stillage was 54,000 mg/L of COD. The CODs of the water after processing in the lignin conversion process was 17,000 mg/L, a 69% reduction of CODs.

Thus, one embodiment of the process will produce an aqueous phase having a COD concentration preferably less than 50% of the COD concentration of the aqueous phase of the lignin feedstock of the lignin conversion process. With less than 40% being more preferred and less than 32% being most preferred.

The aqueous phase can be recycled or reused, with or without further COD removal or reduction of COD concentration, in the carbohydrate conversion step as the soaking water, the water of the steam explosion or other wash water or fermentation streams; or it can be re-used or recycled in the lignin conversion step as part of the slurry creation or make up water.

The re-use or recycle of just 10% of the aqueous phase has massive implications for the waste water treatment, which is a significant part of the expense of operating a carbohydrate conversion process, a lignin conversion process, or an integrated process.

The water from lignin-cellulosic feedstock was removed and visual and analytically evaluated prior to being processed in the lignin conversion process.

This reuse of the water is depicted in FIG. 3, where at least a portion of the water from the reaction is separated from the lignin conversion products and re-used in the process. The water depicted as stream (650) could be used for the slurry at stream (320) or as part of the hydrolysis step at (120) of the carbohydrate conversion or used in the soaking or steam explosion steps of the pre-treatment. If not reused, the water is generally sent to waste water treatment for further purification and re-introduction into the environment.

Analytical Measurements

1. Composition of Lignin-Rich Composition

The composition of lignin-rich composition was determined according to the following standard procedures:

Determination of Structural Carbohydrates and Lignin in Biomass

Laboratory Analytical Procedure (LAP) Issue Date: Apr. 25, 2008

*Technical Report* NREL/TP-510-42618 Revised April 2008

Determination of Extractives in Biomass

Laboratory Analytical Procedure (LAP) Issue Date: Jul. 17, 2005

*Technical Report* NREL/TP-510-42619 January 2008

Preparation of Samples for Compositional Analysis

Laboratory Analytical Procedure (LAP) Issue Date: Sep. 28, 2005

*Technical Report* NREL/TP-510-42620 January 2008

Determination of Total Solids in Biomass and Total Dissolved Solids in Liquid Process Samples Laboratory Analytical Procedure (LAP) Issue Date: Mar. 31, 2008

*Technical Report* NREL/TP-510-42621 Revised March 2008

Determination of Ash in Biomass

Laboratory Analytical Procedure (LAP) Issue Date: Jul. 17, 2005

*Technical Report* NREL/TP-510-42622 January 2008

Determination of Sugars, by Products, and Degradation Products in Liquid Fraction Process Samples Laboratory Analytical Procedure (LAP) Issue Date: Dec. 8, 2006

*Technical Report* NREL/TP-510-42623 January 2008

Determination of Insoluble Solids in Pretreated Biomass Material

Laboratory Analytical Procedure (LAP) Issue Date: Mar. 21, 2008

NREL/TP-510-42627 March 2008

2. Composition of Liquid Products

The composition of liquid products were determined by means of Agilent 7890 Gas chromatogram and Agilent 5975C Mass Detector, according to the following procedure and parameters.

Injector Parameters in the Gas Chromatogram:

Injection volume: 2 ul

Pulsed spilt injection

Injection pulsed pressure: 50 psi for 0.5 min

Temperature: 220° C.

Pressure: 20.386 psi

Septum purge: 3 ml/min

Split ratio: 10:1

Split flow 13 ml/min

Analytical Column:

Column: Restek RXI-5Sil MS, 30 meter, 0.25 mm ID, 0.5 um df

Flow (He): 1.3 ml/min

MSD Transfer Line: (Mass Detector)

Temperature profile: 280° C. for entire run

Column transfer line: HP-101 methyl siloxane-101 methyl siloxane: 12 m×200 um×0.25 um Oven Parameters: (Connected to the Column)

40° C. for 1 min

12° C./min to 220° C. for 0 mins

30° C./min to 300° C. for 17 mins

Detector Parameters:

Temperature: 310° C.

H2 flow: 45 ml/min

Air flow: 450 ml/min

Makeup flow: 26.730 ml/min

MS Acquisition Parameters:

EM voltage: 1871

Low mass: 10

High mass: 350.00

Threshold: 25 samples: 3

MS source: 230° C.

MS quad: 150° C.

Products and related percentage content relative to the weight of liquid products were identified by means of NIST 2008 peak identification software. Only products corresponding to an area greater than 1% of the whole spectrum area are reported.

3. Composition of Solid Products

The filtered solids were dried and then ashed. The burnt portion were considered unreacted lignin. The ash portion was considered nickel catalyst.

4. Composition of Gas Products

The non-condensed gases were identified by gas chromatography.

We claim:

1. A method for separating lignin conversion products from catalyst particles during a continuous catalytic conversion of a lignin feedstock to lignin conversion products comprising the steps of:

a. conducting the continuous catalytic conversion of the lignin feedstock to the lignin conversion products in the presence of free catalyst particles in a lignin conversion reactor, with the lignin conversion reactor having a liquid phase and a gas phase with a liquid level at the interface between the liquid phase and the gas phase, and b. removing the lignin conversion products from the lignin conversion reactor at a lignin conversion products removal velocity at a point in the lignin conversion reactor which is higher relative to gravity than the liquid level of the lignin conversion reactor wherein the lignin conversion products removal velocity is less than a settling velocity of the catalyst particles.

2. The method according to claim 1, wherein the lignin conversion products are removed from the lignin conversion reactor via a dip tube.

3. The method according to claim 1, wherein the lignin conversion products removal velocity is less than the settling velocity of at least 75% by weight of the catalyst particles.

4. The method according to claim 2, wherein the lignin conversion products removal velocity is less than the settling velocity of at least 75% by weight of the catalyst particles.

5. The method according to claim 1, wherein the lignin conversion products removal velocity is less than the settling velocity of at least 85% by weight of the catalyst particles.

6. The method according to claim 2, wherein the lignin conversion products removal velocity is less than the settling velocity of at least 85% by weight of the catalyst particles.

7. The method according to claim 1, wherein the lignin conversion products removal velocity is less than the settling velocity of at least 90% by weight by weight of the catalyst particles.

8. The method according to claim 2, wherein the lignin conversion products removal velocity is less than the settling velocity of at least 90% by weight of the catalyst particles.

9. The method according to claim 1, wherein the lignin conversion products removal velocity is less than the settling velocity of at least 95% by weight of the catalyst particles.

10. The method according to claim 2, wherein the lignin conversion products removal velocity is less than the settling velocity of at least 95% by weight of the catalyst particles.

11. The method according to claim 1, wherein the lignin conversion products removal velocity is less than the settling velocity of 100% by weight of the catalyst particles.

12. The method according to claim 2, wherein the lignin conversion products removal velocity is less than the settling velocity of 100% by weight of the catalyst particles.

13. The method according to claim 1, wherein the continuous catalytic conversion is conducted at a temperature in the range of 190° C. to 370° C.

14. The method according to claim 2, wherein the continuous catalytic conversion is conducted at a temperature in the range of 190° C. to 370° C.

15. The method according to claim 1, wherein the catalyst particles are sponge elemental catalyst particles comprising a metal selected from the group consisting of palladium, platinum, nickel, ruthenium, rhodium, molybdenum, cobalt, and iron.

16. The method according to claim 2, wherein the catalyst particles are sponge elemental catalyst particles comprising a metal selected from the group consisting of palladium, platinum, nickel, ruthenium, rhodium, molybdenum, cobalt, and iron.

17. The method according to claim 1, wherein the catalyst particles are sponge elemental catalyst particles comprising nickel.

18. The method according to claim 2, wherein the catalyst particles are sponge elemental catalyst particles comprising nickel.

* * * * *